(12) United States Patent
Lee et al.

(10) Patent No.: US 8,690,840 B2
(45) Date of Patent: Apr. 8, 2014

(54) TIME-SELECTIVE BIORESORBABLE OR COLLAPSIBLE DRUG DELIVERY SYSTEMS AND METHODS

(75) Inventors: Heejin Lee, Arlington, MA (US); Michael J. Cima, Winchester, MA (US); Cheryl Larrivee-Elkins, Framingham, MA (US); Dennis Giesing, Lee's Summit, MO (US); Jessica K. Anderson, Boston, MA (US); Sarma Duddu, Concord, MA (US)

(73) Assignee: TARIS Biomedical, Inc., Lexington, MA (US)

( * ) Notice: Subject to any disclaimer, the term of this patent is extended or adjusted under 35 U.S.C. 154(b) by 211 days.

(21) Appl. No.: 13/267,560

(22) Filed: Oct. 6, 2011

(65) Prior Publication Data

US 2012/0089122 A1    Apr. 12, 2012

Related U.S. Application Data

(60) Provisional application No. 61/390,549, filed on Oct. 6, 2010, provisional application No. 61/405,379, filed on Oct. 21, 2010.

(51) Int. Cl.
*A61M 31/00* (2006.01)
(52) U.S. Cl.
USPC ............................................ 604/285; 604/517
(58) Field of Classification Search
USPC ...................... 604/57, 285, 287, 288, 517
See application file for complete search history.

(56) References Cited

U.S. PATENT DOCUMENTS

| 4,871,542 | A | 10/1989 | Vilhardt |
| 5,062,829 | A | 11/1991 | Pryor et al. |
| 5,516,522 | A | 5/1996 | Peyman et al. |
| 6,039,967 | A | 3/2000 | Ottoboni et al. |
| 6,171,298 | B1 | 1/2001 | Matsuura et al. |
| 6,183,461 | B1 | 2/2001 | Matsuura et al. |
| 2003/0077310 | A1* | 4/2003 | Pathak et al. ............... 424/423 |
| 2003/0118649 | A1 | 6/2003 | Gao et al. |
| 2006/0105010 | A1 | 5/2006 | Rahe et al. |
| 2006/0264912 | A1 | 11/2006 | McIntyre et al. |
| 2007/0202151 | A1 | 8/2007 | Lee et al. |
| 2009/0149833 | A1 | 6/2009 | Cima et al. |
| 2010/0003297 | A1 | 1/2010 | Tobias et al. |
| 2010/0330149 | A1 | 12/2010 | Daniel et al. |
| 2010/0331770 | A1 | 12/2010 | Lee et al. |
| 2011/0152839 | A1 | 6/2011 | Cima et al. |

FOREIGN PATENT DOCUMENTS

| EP | 0 572 932 B1 | 9/2000 |
| WO | 2004037318 A2 | 5/2004 |
| WO | 2012018923 A1 | 2/2012 |
| WO | 2012019155 A1 | 2/2012 |

* cited by examiner

*Primary Examiner* — Emily Schmidt
(74) *Attorney, Agent, or Firm* — Sutherland Asbill & Brennan LLP

(57) ABSTRACT

Implantable medical devices and treatment methods are provided, particularly for use in the bladder. The device is configured for retention in the bladder for at least a portion of the drug delivery period and includes at least one biodegradable component such that following a biodegradation at a selected time, the retention function is lost and the device or portions thereof are resorbed and/or excreted. The method may include deploying into the bladder of a patient a device having a device structure housing a drug formulation comprising at a drug; releasing drug from the device structure into the bladder; and then, changing the composition of urine in the bladder, e.g., by altering the pH, to trigger degradation of at least part of the device structure to enable the device structure or parts thereof to be excreted from the bladder.

25 Claims, 10 Drawing Sheets

IN RETENTION SHAPE READY FOR VOIDING

TIME-SELECTIVE BIORESORBABLE OR COLLAPSIBLE DRUG DELIVERY SYSTEMS AND METHODS

CROSS-REFERENCE TO RELATED APPLICATIONS

This application claims priority to U.S. Provisional Patent Application No. 61/390,549, filed Oct. 6, 2010, and U.S. Provisional Patent Application No. 61/405,379, filed Oct. 21, 2010, which are incorporated herein by reference.

BACKGROUND

The present disclosure is generally in the field of implantable medical devices, and more particularly relates to systems and methods of selectively removing a drug delivery device from a body cavity or lumen, such as the bladder.

U.S. Patent Application Publication No. 2007/0202151 and No. 2009/0149833 describe drug delivery devices for minimally invasive deployment and retention in a cavity or lumen of a patient, such as the bladder. The device may be configurable into a relatively low profile for minimally invasive deployment into the patient's body, and once implanted may spontaneously assume, or be configured to take, a relatively expanded profile to cause the device to be resistant to excretion and retained in the bladder over the course of delivering its drug payload to the body of the patient. In one embodiment, the patient subsequently must undergo an additional medical procedure to retrieve the drug-depleted device from the patient's body. Alternatively, a retrieval string may be attached to the deployed device to run transurethrally, but this is not viable for longer periods of deployment to due the risk of infection and/or inadvertent dislodgement.

It therefore would be desirable to provide devices and methods that avoid the necessity of retrieving the drug delivery device after the drug payload has been released from the device. It also would be desirable to facilitate selective removal of the device from the patient's bladder.

SUMMARY

In one aspect, an implantable medical device for controlled drug delivery is provided that includes a drug formulation and a device structure that is deformable between a retention shape and a low profile shape for deployment in the bladder of a patient. The device structure includes at least one drug reservoir lumen into which the drug formulation is positioned. In some embodiments, the device structure has at least one non-degradable portion and at least one degradable link that is configured to degrade at a selected time in vivo to cause the device structure to lose the retention shape, e.g., collapse, so that the at least one non-degradable portion is excretable from the bladder. In other embodiments, the device structure includes at least one portion that is degradable upon contact with a physiological fluid adjacent to the device structure when deployed in vivo following the selective alteration of the composition of the physiological fluid adjacent to the device structure, the degradation of the at least one portion being effective to cause the device structure to lose the retention shape so that the device is excretable from the bladder.

In another aspect, methods are provided for the delivery of a drug to a patient that include deploying into the bladder of the patient through the urethra a device having a device structure housing a drug formulation of at least one drug, releasing at least a portion of the drug from the device structure into the bladder, and then changing the composition of urine in the bladder to trigger degradation of at least part of the device structure to enable the device structure or parts thereof to be excreted from the bladder.

DETAILED DESCRIPTION

Figure 1:
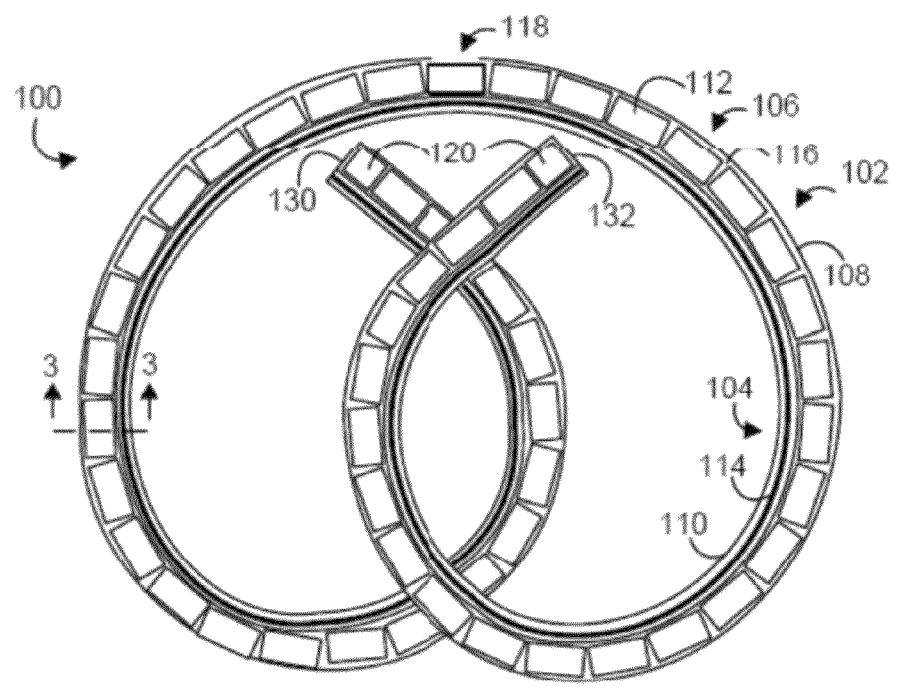
FIG. 1 is a plan view of an embodiment of a drug delivery device.

Implantable devices are provided that can be deployed, or implanted, into a lumen or body cavity of a patient, such as the bladder or another genitourinary site, for release of one or more drugs over an extended period.

The device may be deployed through a deployment instrument, such as a catheter or cystoscope, positioned in the urethra. The device is released into the bladder, and then drug is released from the device over an extended period. Advantageously, the device is configured so that it self-eliminates from the body so that an invasive retrieval procedure is unnecessary.

The self-eliminating device includes a device structure that is at least partially biodegradable. The device structure partially or completely degrades over a period of elimination, the onset of which is controlled or preprogrammed into the device. By controlling the onset of the period of elimination, the timing of the elimination of the device structure is controlled. For example, the device structure may be eliminated through complete or substantial degradation or resorption, through partial degradation of the device structure to form excretable pieces, through partial degradation of a retention feature such that the device structure assumes a shape suitable for excretion, or combinations thereof.

The implantable device is designed for deployment into and retention within the bladder. In a preferred embodiment, the device is flexible so that the device can be deformed for insertion, yet once implanted the device may resist excretion in response to the forces of urination or other forces. In particular embodiments, the drug delivery device is small enough to be inserted through a deployment instrument extending through the urethra into the bladder. Examples of suitable deployment instruments and techniques are described in U.S. Patent Application Publication No. 2011/0202036 to Boyko, et al., which is incorporated herein by reference. The devices and methods disclosed herein may be used in humans, whether male or female, adult or child, or in other mammals, such as for veterinary or livestock applications.

The devices and methods disclosed herein build upon those described in U.S. application Ser. No. 12/333,182, filed Dec. 11, 2008; U.S. application Ser. No. 12/825,215, filed Jun. 28, 2010; and U.S. application Ser. No. 12/972,364, filed Dec. 17, 2010, which are incorporated by reference herein. In one embodiment, the drug delivery device may deliver lidocaine or another anesthetic agent locally to the bladder over an extended period for the treatment of a condition such as IC/PBS, neurogenic bladder, or pain such as post-operative pain.

I. Elimination of the Implantable Drug Delivery Device

Generally, the implantable drug delivery devices include a drug formulation and a device structure. For purposes of this disclosure, the term "the device structure" generally refers to portions of the device other than the drug formulation. In the embodiment shown in FIGS. 1-3, for example, the device structure includes the device body 106, the retention frame 114, and any other components of the device 100 other than the drug formulation, such as any sealing plugs 120, any adhesive or filling materials used to construct or stabilize the device, and any radio-opaque portions used to facilitate detection of the device in the body. In such embodiments, the device structure may include the entire device 100 except for the solid drug tablets 112, which may be substantially or completely solubilized and released in vivo.

The device structure may be configured so that its elimination from the bladder may be initiated at a preselected time or within a preselected time window following implantation. The elimination of the device structure also may initiate in response to a change in the composition or characteristics of any fluid about the device, such as a change in the pH, temperature, pressure, or ionic strength of urine about the exterior of the device, within the interior of the device, or some combination thereof. The change in composition or characteristics may be initiated from either within the device or from within the implantation environment, in response to either the duration of exposure to physiological fluids in vivo or the introduction of an external agent into the implantation environment.

Controlling the onset of elimination permits delaying elimination of the device structure until after the device has substantially or completely released the drug. The elimination period may not be initiated until after the drug delivery period has ended or neared its end. Thus, the device may experience an initial period of drug release and a subsequent period of elimination, which may be controlled to overlap insignificantly or not at all. However, the drug release and elimination periods may partially or completely overlap, such as in embodiments in which the device begins degrading during drug release. For example, some remnants of solubilized drug or even portions of the drug formulation may remain in the device even as the device structure begins degrading. In cases in which the device structure degrades relatively slowly, it may be acceptable or even desirable to initiate degradation of the device structure before the drug has completely vacated the device.

Upon initiation of the elimination period, biodegradable portions of the device structure begin degrading. In some embodiments, the entire device structure is biodegradable. Over the period of degradation, the entire device structure degrades into remnants that are resorbed or excreted by the body. For example, both the device body and the retention frame may be substantially or completely biodegradable. Any sealing plugs, adhesives, or other materials used to construct the device also may be biodegradable.

As used herein, the term "bioerodible" or "biodegradable" means that the device, or part thereof, degrades in vivo by dissolution, enzymatic hydrolysis, erosion, resorption, or a combination thereof. In one embodiment, this degradation occurs at a time that does not interfere with the intended kinetics of release of the drug from the device. For example, substantial erosion of the device may not occur until after the drug formulation is substantially or completely released. In one embodiment, the device is erodible and the release of the drug formulation is controlled at least in part by the degradation or erosion characteristics of the erodible device body.

In other embodiments, at least a portion of the device structure is not biodegradable and is excreted from the body substantially intact. Upon degradation of the biodegradable portions of the device structure, the non-biodegradable portion may experience a change in size, shape, or configuration that enables the non-biodegradable portion to be excreted from the body. In embodiments, the device structure includes at least one non-degradable portion and least one degradable link that is configured to degrade at a selected time in vivo to cause the device structure to lose its retention shape so that the at least one non-degradable portion is excretable from the bladder.

For example, the non-biodegradable portion may be joined to or confined within the remainder of the device structure by a biodegradable portion, and upon degradation of the biodegradable portion, the non-biodegradable portion is released or separated from the remainder of the device structure for excretion. In embodiments, the biodegradable portions include links associated with one or more non-biodegradable portions. Once separated from the remainder of the device structure, the non-biodegradable portion may have a size, shape, and configuration that is suited for excretion from the body.

One example of such a configuration is an embodiment in which the device structure is configured to separate into two or more non-degradable segments, each segment sized and shaped to be excretable from the bladder, upon degradation of at least one degradable link that connects the two or more non-degradable segments. In this embodiment, the non-biodegradable portions are joined together by degradable links, such that the device body as a whole is relatively larger. Upon degradation of the links, the device body may break into multiple discrete pieces for excretion from the body.

Another example of such a configuration is an embodiment in which the entire device structure is biodegradable except for certain non-biodegradable components, such as a sealing plug or a radiopaque marker. The sealing plug or marker may be retained in the device structure, but upon degradation of the device structure, the sealing plug or marker may be released for excretion. In such a case, the sealing plug or marker is sized for excretion from the body so that once the sealing plug or marker is separated from the remainder of the device, the sealing plug or marker is readily excreted.

Another example of such a configuration is an embodiment in which the device structure is configured to assume, upon degradation of at least one degradable link, a flexible elongated shape that is excretable from the bladder. In one particular embodiment, the retention frame is configured, upon degradation of the at least one degradable link, to cease imparting the retention shape to the device structure. The degradation of the links causes the device structure to assume an elongated shape that is suited for excretion from the body.

In some embodiments, the time at which the bioerosion process is initiated can be controlled by selectively altering the composition of a physiological fluid adjacent to or within the device, such as urine. In embodiments, the device comprises a body that dissolves or erodes in viva upon a selective alteration in the composition of urine in the bladder. For example, the composition of urine may be changed by changing the pH, or introducing a catalyst or chelating agent into the bladder.

In some embodiments, the pH of the bladder environment (i.e., the urine) may be changed by introducing a material in the bladder that changes the composition of the urine adjacent to or within the device. The introduction of the material may be by oral administration. The material also may be introduced into the bladder via catheter through the urethra, with deployment of the drug delivery device or in a separate, later procedure. For example, the pH of the bladder environment may be changed upon the introduction of a pH-changing agent into the bladder or in response to a particular diet of the patient. Suitable drugs or supplements also may be administered to the patient to change the pH of urine. Thereafter, the exposure of the exterior surfaces of the device to the pH of the bladder environment may cause the device to degrade. In embodiments in which the device is water permeable, a change in the pH of the bladder environment may also affect the pH of fluid within the device, such that the device also degrades due to exposure of its interior surfaces to altered pH. In these embodiments, at least a portion of the device structure is formed of a material selected to degrade following a selected change in the pH of the physiological fluid adjacent to the device, such as urine.

In other embodiments, the composition of a physiological fluid adjacent to or within the device may be changed from within the device. In embodiments, the device structure is associated with at least one fluid-altering agent effective to cause the selective alteration of the composition of the physiological fluid, adjacent to or within the device. In one embodiment, the at least one fluid-altering agent is contained in at least one solid unit operable to release the fluid-altering agent into the physiological fluid upon conclusion of a release delay period. The solid unit can be coated or encapsulated with a release delaying material. In certain embodiments, the fluid-altering agent comprises one or more of the following: a pH-altering agent, a chelating agent, or a catalyst.

In some embodiments, the fluid-altering agent may comprise a pH-altering agent that changes the pH of the physiological fluid adjacent to or within the device from a first pH to a second pH; and at least one degradable portion of the device structure comprises at least one pH-responsive material that is stable in the presence of a fluid having the first pH and degrades in the presence of a fluid having the second pH.

For example, the device may house one or more release delayed, pH-altering pills. Examples include tablets having a pH-altering substance coated in a release delaying coating or a capsule having a pH-altering substance encapsulated in a release delayed capsule. The coating or capsule degrades or dissolves over a pre-selected period of time, controlling or delaying release of the pH-altering substance. Examples of suitable release delaying materials include enteric coating materials known in the art, such as those used in oral administration. For example, release of the pH-altering substance may be delayed until after most or all of the drug has been released. As the drug is released, the drug may be replaced with water or urine, such that the device houses primarily water or urine after most or all of the drug is released. The pH-altering pill may alter the pH of the water or urine within the device upon degradation or dissolution of its coating or encapsulation, causing the device to degrade from within. In particular, the device may degrade due to the exposure of its interior surfaces to the pH within the device. In embodiments in which the device is water permeable, the pH-altering pill also may affect the pH within the bladder, such that the device also degrades due to exposure of its exterior surfaces to altered pH. However, the device may primarily degrade from the inside out, as the relatively small volume of fluid within the device is maintained in close proximity to the device structure, keeping the concentrated high (or low) pH fluid within the device from becoming diluted with the potentially large volume of urine outside of the device.

In some embodiments, the device body or housing may comprise a pH sensitive or pH responsive polymer or copolymer. In some embodiments, the material may comprise ionizable functional groups in which charge is generated in response to pH. For example, the material may have functional groups which may ionize and acquire a positive or negative charge in a certain pH, such as —COOH, —NH$_2$ groups. The change in charge may result in changes in the electrostatic forces within the material, enabling the erosion or dissolution of the material.

For example, the material may comprise natural materials such as the polysaccharides chitosan, alginate, and k-carrageenan. The material also may comprise synthetic polymers or gels that are pH sensitive including polyethleneimine, polylysine, poly-N,N-dimethyl aminoethyl methacrylamide, polyacryclid acid, or polymethacrylic acid (PMAA). The material may comprise PMAA and poly(ethlyene) glycol copolymers, poly(acrylic acid-co-octyl acrylate), poly(methacrylic acid-co-ethacrylic acid) PIMA-co-EA), 4-amino-N-(4,6-dimethyl-2-pyridinyl)benzene sulfonamide-N,N-dimethyl acrylamide, and poly-N-acryloyl-N-propylpiperazine (PNANP). In some embodiments, the material may comprise polymers or copolymers that in a non-ionized state are hydrophobic and water insoluble, and in an ionized state are water soluble.

In some embodiments, the drug delivery device may comprise a housing comprising a material that will degrade or erode when contacted by an enzyme or other catalyst. For example, the housing may comprise a material that will undergo hydrolysis in the presence of an enzyme. The enzyme may be naturally produced by the patient, may be produced by the patient in response to a substance administered to the patient, may be administered to the patient at or near the end of treatment, e.g., administered directly into the bladder (or other body lumen) where the device is placed, or stored on-board the delivery device. In one case, an enzyme is introduced into the bladder by an instillation procedure. In another case, the enzyme is stored in a tablet coated in a time-delaying coating.

There are a number of urinary enzymes found in humans and in animals. See Raab, W. P., "Diagnostic Value of Urinary Enzyme Determinations" *Clinical Chemistry* 18 (1):5-25 (1972). These may be from serum, kidneys, epithelial cells of the urogenital tract, or glandular secretions of the orogenital tract. Activators and inhibitors for such enzymes are also known to be found in urine. Examples of enzymes found in urine include amylase (normal range 2.6-21.2 IU), lactic dehydrogenase (17.5 mU/ml), leucine amino-peptidase (2 to 18 u/24 hr), urokinase (normal level 2068±28 u/ml). The amounts of these or other enzymes in the urine in the bladder may be increased, for example, by instilling a particular dose and/or including the enzyme on-board the drug delivery device.

In another embodiment, a chelating agent is used to bind to an inhibitory ion which then allows an enzyme to degrade a polymeric housing material. The device also may dissolve or erode in response to the presence of an enzyme in the patient's urine, which may be introduced into the urine, may be naturally produced in vivo in response to the introduction of another substance into the urine, or may already be present in the urine but becomes effective to dissolve or erode the device upon the introduction of a chelating agent into the urine. Therefore, in some embodiments, at least a portion of the device structure is formed of a material selected to degrade following introduction of a chelating agent, into the physiological fluid adjacent to the device, that is effective to bind to an inhibitory ion which then allows an enzyme to degrade at least one portion of the device structure. For example, iron or another metal might be required to stabilize a polymer used to construct the device housing. The administered chelator may remove the iron and thereby cause the polymer to degrade. The chelating agent may be orally administered or delivered by an instillation procedure or stored on-board the drug delivery device (e.g., temporarily isolated from the degradable polymer, such as within a tablet coated in a release delaying coating).

II. The Implantable Medical Device

Generally, the implantable medical device includes a device structure and a drug formulation containing at least one drug.

In some embodiments, the device structure includes a drug reservoir portion and a retention frame portion. The drug reservoir portion includes a drug reservoir lumen into which the drug formulation is positioned. The retention frame portion, in some embodiments, includes a retention frame and a retention frame lumen, the retention frame being positioned at least partially within the retention frame lumen. In other embodiments, the retention frame portion includes a retention frame only. The device structure may include a device body that defines the drug reservoir lumen and the retention frame lumen.

In other embodiments, the device structure includes a drug reservoir portion, but no retention frame portion. In these embodiments, the drug reservoir portion is made from a material capable of imparting a retention shape to the device.

In some embodiments, the device structure is entirely biodegradable. In other embodiments, the device structure includes at least one biodegradable portion and at least one non-degradable portion. In particular embodiments, the device structure comprises at least one non-degradable portion and at least one degradable link. In one embodiment the resorbable or degradable links are positioned in the drug reservoir portion, for example, the drug reservoir lumen. In another embodiment, the resorbable or degradable links are positioned in the retention frame portion, for example, the retention frame lumen.

An embodiment of a drug delivery device 100 is illustrated in FIG. 1. The device 100 includes a drug reservoir portion 102 and a retention frame portion 104. In FIG. 1, the device 100 is shown in a relatively expanded shape suited for retention in the body, especially the bladder, and in FIG. 2 the device 100 is shown in a relatively lower-profile shape for deployment through the channel 202 of a deployment instrument 200, such as a cystoscope or catheter. Following deployment into the body, the device 100 may assume the relatively expanded shape to retain the drug delivery device in the body cavity or lumen, such as the bladder.

For the purposes of this disclosure, terms such as "relatively expanded shape," "relatively higher-profile shape," or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape," "low-profile shape," or "deployment shape" generally denote any shape suited for deploying the drug delivery device into the body, including the linear or elongated shape shown in FIG. 2 that is suited for deploying the device through the working channel of a catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body. Once deployed, the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

In particular, the drug delivery device 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 3:
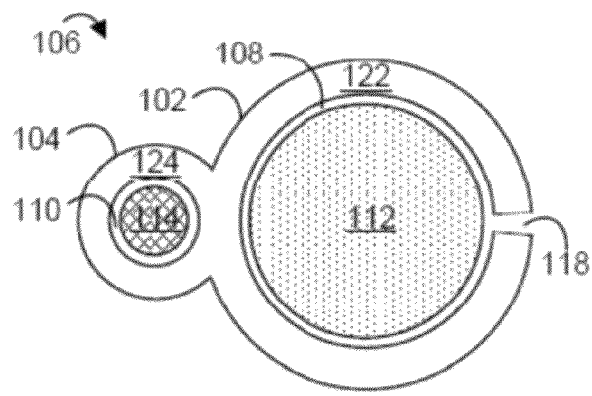
FIG. 3 is a cross-sectional view of the drug delivery device shown in FIG. 1, taken along line 3-3 in FIG. 1.

As shown in the cross-sectional view of FIG. 3, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment may be used, as shown, for example, in FIG. 4.

An aperture 118 may be formed through the wall 122 that defines the drug reservoir lumen 108. The aperture 118 may provide a passageway for releasing drug from the drug reservoir lumen 108 as further described below. However, the aperture 118 may be omitted in some embodiments.

As shown in FIG. 1, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, any number of drug units may be used. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly. Once the drug units 112 are loaded, at least two end plugs 120 block the entry 130 and exit 132. The end plugs 120 may be cylindrical plugs inserted into the entry 130 and the exit 132, each having a slightly larger outer diameter than an inner diameter of the drug reservoir lumen 108 so that the plugs substantially enclose the entry 130 and exit 132 and are snugly retained in position. In some cases, a number of end plugs 120 can be positioned in the entry 130 or the exit 132. The end plugs 120 may be silicone plugs. The end plugs 120 also may be omitted, in which case the entry 130 and exit 132 may be closed with a material, such as adhesive, that is placed in the drug reservoir lumen 108 in workable form and cures therein.

In some embodiments, the drug tablets 112 may not fill the entire drug reservoir lumen 108. In such embodiments, a filling material may be used to fill the remainder of the drug reservoir lumen 108. For example, the drug tablets 112 may be loaded in a central portion of the drug reservoir lumen 108 and the filling material may be loaded in the remaining end portions of the drug reservoir lumen 108. The filling material may be inserted into the end portions of the drug reservoir lumen 108 after the lumen is filled with the drug tablets 112. The filling material may be a polymeric material. The polymeric material may be placed in the drug reservoir lumen 108 in workable form and may cure therein. Suitable polymeric materials may cure at room temperature or in response to an external stimulus, such as heat. In some cases, the filling material may enclose the entry 130 and exit 132, in which case the end plugs 120 may or may not be provided. The filling material also may be a number of end plugs 120 inserted into the end portions of the drug reservoir lumen 108.

Once the drug units 112 are loaded, interstices 116 or breaks may be formed between adjacent drug units 112. The drug delivery device 100 may be relatively flexible or deformable despite being loaded with a solid drug, as each drug unit 112 may be permitted to move with reference to adjacent drug units 112. Along the length of the drug reservoir lumen 108, the drug units 112 may have the same composition or may vary in composition, and in some cases drug units 112 of different compositions may be in distinct reservoirs that are segregated, either axially or radially, along the length of the drug reservoir lumen 108.

The retention frame lumen 110 is loaded with the retention frame 114, which may be an elastic wire. The retention frame 110 may be configured to spontaneously return to a retention shape, such as the illustrated "pretzel" shape or another coiled shape. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-Profile shape within the body in response to expected forces, such as the hydrodynamic forces associated with contraction of the detrusor muscle and urination. Thus, the device 100 may be retained in the body once implanted, limiting or preventing accidental expulsion.

The material used to form the device body 106 may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The flexible material also allows the device body 106 to flex outward or circumferentially expand in response to a flow of pressurized gas through the drug reservoir lumen 108 during drug loading, as described below. The material used to form the device body 106 also may be water permeable or porous so that solubilizing fluid can enter the drug reservoir portion 102 to solubilize the drug units 112 once the device is implanted. For example, silicone or another biocompatible elastomeric material may be used.

In embodiments, the drug delivery device 100 of FIG. 1 is formed entirely from biodegradable materials. In other embodiments, the drug reservoir lumen 108 is formed from non-degradable materials, and the retention frame lumen 110 and retention frame 114 are formed form degradable materials. In further embodiments, the drug reservoir lumen 108 and retention frame lumen 110 are formed from non-degradable materials and the retention frame 114 is formed from a degradable material.

Figure 4:
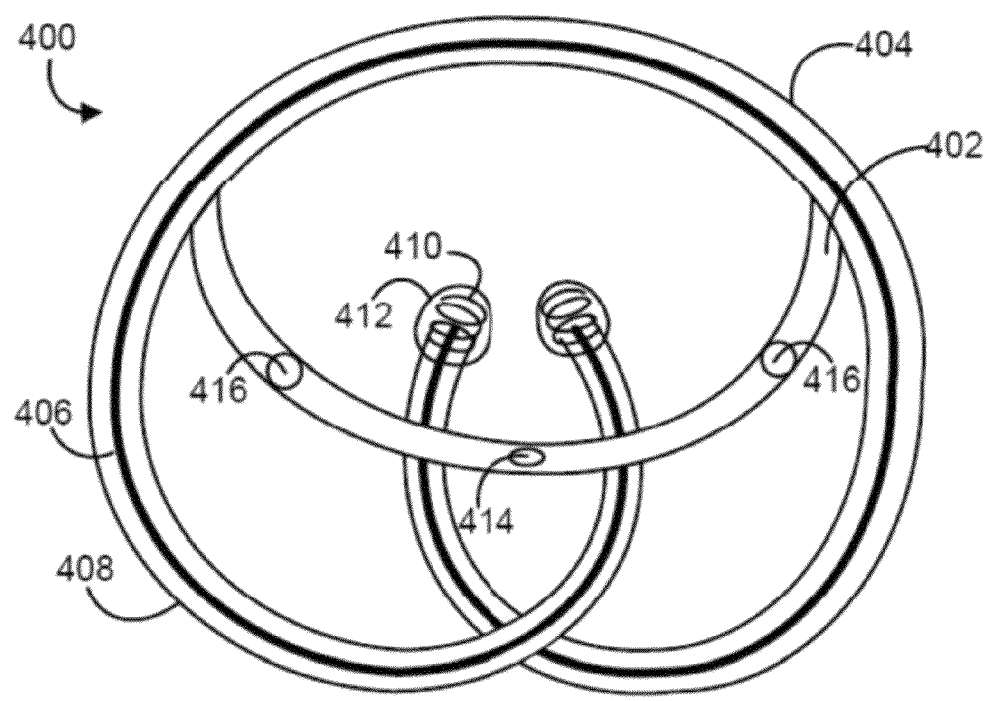
FIG. 4 is a plan view of an embodiment of a drug delivery device.

Another embodiment of a drug delivery device 400 is shown in FIG. 4. The device 400 includes a drug reservoir lumen 402 and a retention frame lumen 404. The drug reservoir lumen 402 is attached to discrete points on the retention frame lumen 404 but is otherwise separate or spaced apart from the retention frame lumen 404. In the drug reservoir lumen 402 are ball-shaped sealing structures 416 designed for retaining the drug (not shown) in the drug reservoir lumen 402. The retention frame 406 is disposed within the retention frame lumen 404. The retention frame lumen 404 is also coated with a polymer coating 408, which may be designed to control the onset of the elimination period. In FIG. 4, the device 400 is shown in a relatively expanded shape suited for retention in the body, and in FIG. 5 the device 400 is shown in a relatively lower-profile shape for deployment through the channel 500 of a deployment instrument, such as a cystoscope or other catheter. Following deployment into the body, the device 400 may assume the relatively expanded shape to retain the drug delivery device in the bladder.

In embodiments, the drug delivery device 400 of FIG. 4 is formed entirely from biodegradable materials, with the exception of the platinum wires, which may be omitted. In other embodiments, the drug reservoir lumen 402 is formed from non-degradable materials, and the retention frame lumen 404 and retention frame 406 are formed form degradable materials. In further embodiments, the drug reservoir lumen 402 and retention frame lumen 404 are formed from non-degradable materials and the retention frame 406 is formed from a degradable material.

Figure 11A:
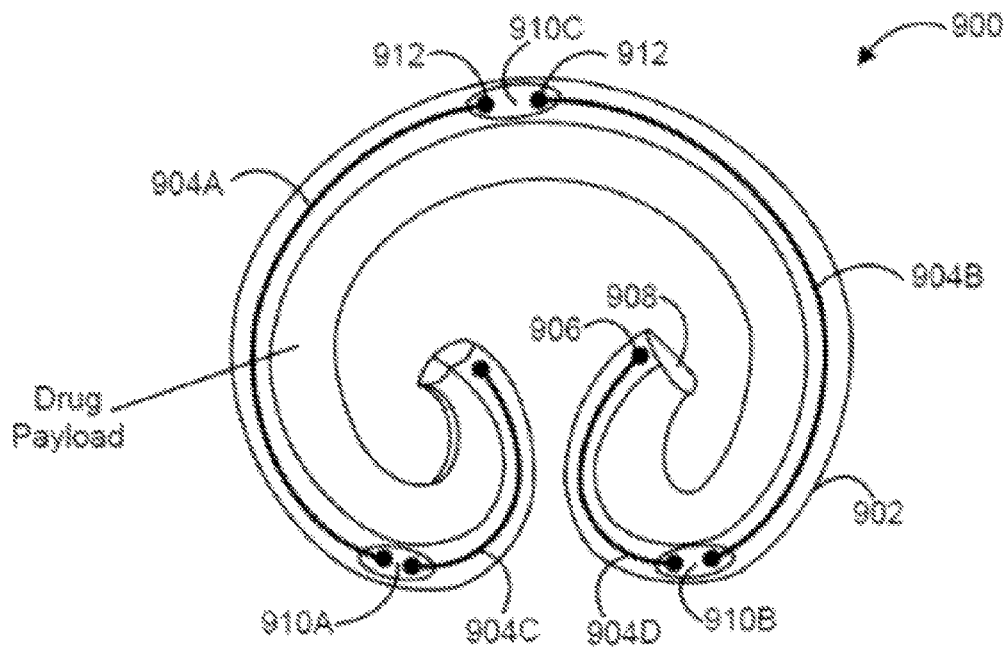
FIGS. 11A-B are plan views of one embodiment of the drug delivery device in its retention shape (FIG. 11A) and in a shape suitable for tolerable voiding (FIG. 11B).
Figure 11B:
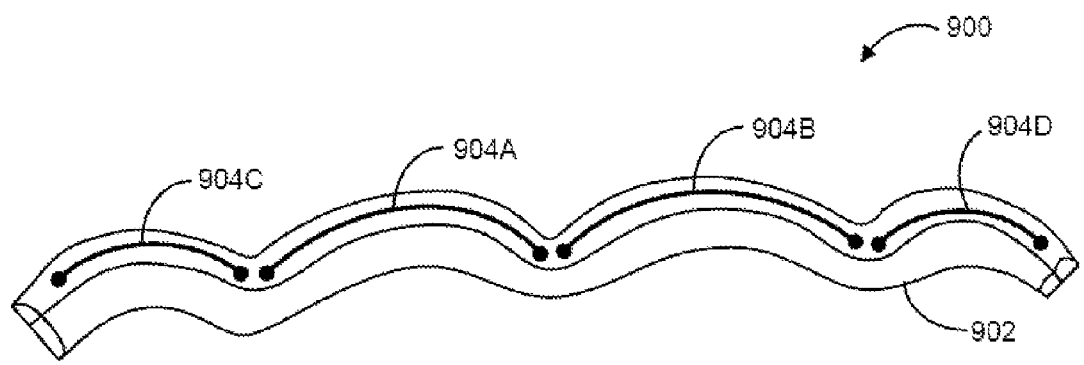

One embodiment of the device is shown in FIGS. 11A-B. In FIG. 11A, device 900 includes a device body 902 and a retention frame 904. The retention frame consists of four wire segments 904A, 904B, 904C, and 904D that are connected by resorbable links 910A, 910B, and 910C. The links connect two adjacent wire segments. The ends of the wire segments include rounded or blunt end caps 912 so that the segment has no sharp ends or edges that could negate the tolerability of the segment within the bladder or during voiding. The end caps 912 may also facilitate securement of the wire segments together with the resorbable links. The device body 902 is in the form of a dual lumen elastomeric tube, which includes a retention frame lumen 906 and a drug reservoir lumen 908, which contains a drug payload (not shown) for release.

In one embodiment, the reservoir portion is formed of silicone and has two lumens, a smaller lumen for the retention wire and a larger lumen for the drug formulation.

In one embodiment, the wire segments are made of nitinol. Other biocompatible materials may be used to form the retention frame and wire segments. In one embodiment, the entire retention frame may be constructed of a resorbable material. In this case, holes in the wire lumen may be provided for the degradable material to be released out of the silicone tubing. In one example, the device may be directly implanted in the bladder during another invasive urological surgical procedure, which is useful when the wire form entirely made of degradable polymer does not have enough elastic property to be passed through the catheter of cystoscope for minimally invasive deployment.

The number of wire segments and links can vary. With a device embodiment having a retention frame that consists of multiple wire segments and multiple links, each segment will undergo less strain when stretched during the device deployment procedure as compared to a device embodiment having a retention frame that consists of only two wire segments and a single link.

The degradable links will eventually fail in vivo as a means to join adjacent wire segments. The particular choice of material and thickness of the link will determine how rapidly the link will fail in vivo. Following link failure, the elastomeric tube (e.g., the silicone reservoir portion) will easily bend at the junctions where the degradable links were initially placed, but the device will remain a single structure since the wire segments remain still within the small lumen. At this point, the device will no longer be able to stay in the bladder, and the shape of the device can be tortuous and overall linear.

Figure 11C:
FIG. 11C is an illustration of a wire segment that is suitable for spontaneous voiding from a bladder where the urethra has a diameter x.

As shown in FIG. 11A, the device initially has a relatively higher profile that facilitates retention of the device during delivery of the drug. As shown in FIG. 11B, following degradation/resorption of the links, the device assumes a relatively lower profile shape that is suitable for voiding of the device. FIG. 11C shows a wire segment that it is suitable for spontaneous voiding from a bladder where the urethra has a diameter x.

As the urethra (about 6 to 8 mm) is larger in diameter than the ureter (about 3 to 4 mm), an object larger than 5 mm in diameter can pass spontaneously when the object is initially situated in the bladder. Objects whose apparent diameter is slightly larger than the urethra diameter can pass spontaneously through the urethra considering the distensible nature of the urethra and hydrodynamic drag associated with bladder contraction and urine flow. Besides the size, the shape and surface roughness and pattern of an object can affect how easily the object in the bladder passes through the urethra or how tolerable the object is upon voiding. Accordingly, in a preferred embodiment, the wire segment alone or with any surrounding tubing has, following resorption of the links, a height x that is 5 mm or less. One therefore can vary the number and length of the wire segments (and the number and length of the links) to achieve a suitable retention shape for the device while also achieving a suitable size and shape for tolerable voiding of the device following resorption of the links. These principles may be applied to the other embodiments described herein.

Figure 12A:
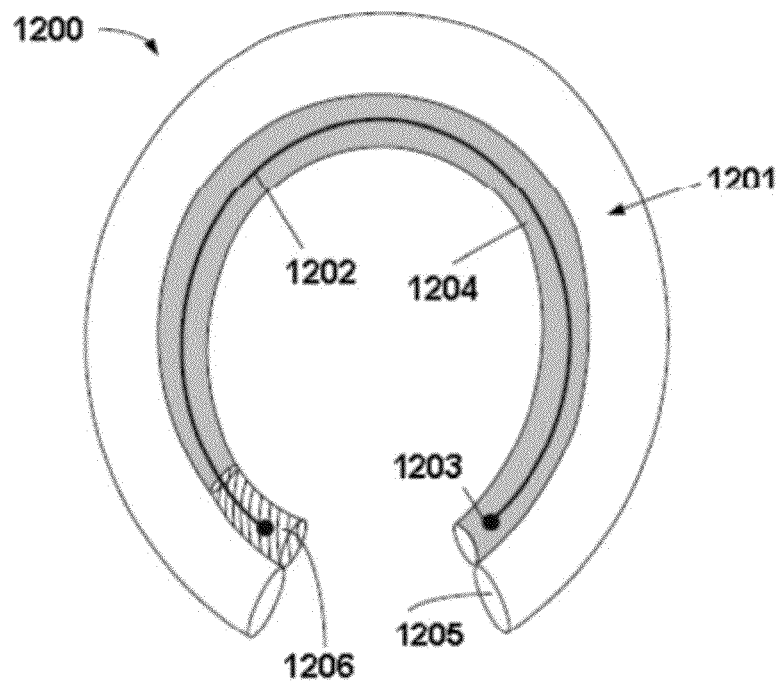
FIGS. 12A-C are plan views of one embodiment of the drug delivery device in its retention shape (FIG. 12A), as the resorbable portion degrades (FIG. 12B), and in a shape suitable for tolerable voiding (FIG. 12C).
Figure 12B:
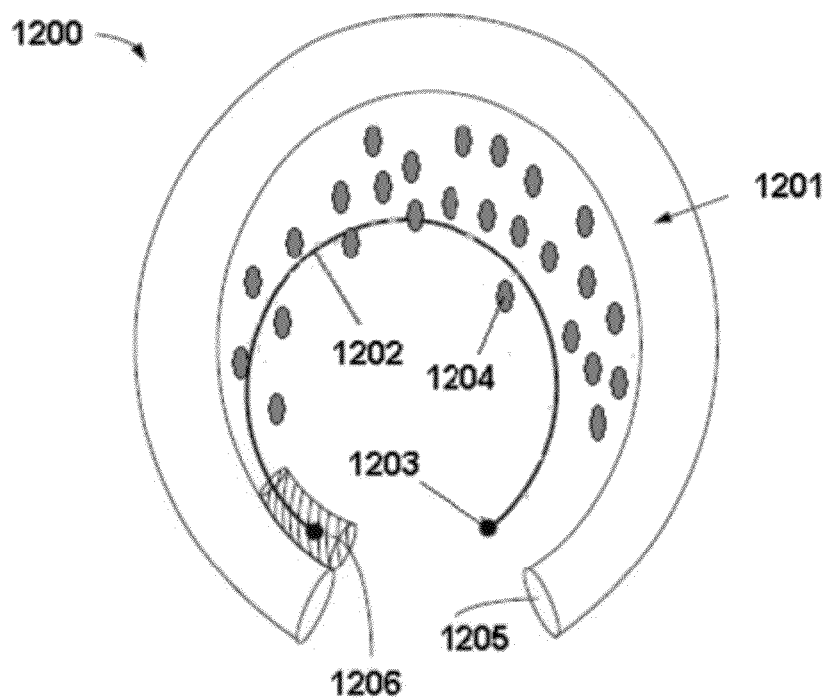
Figure 12C:
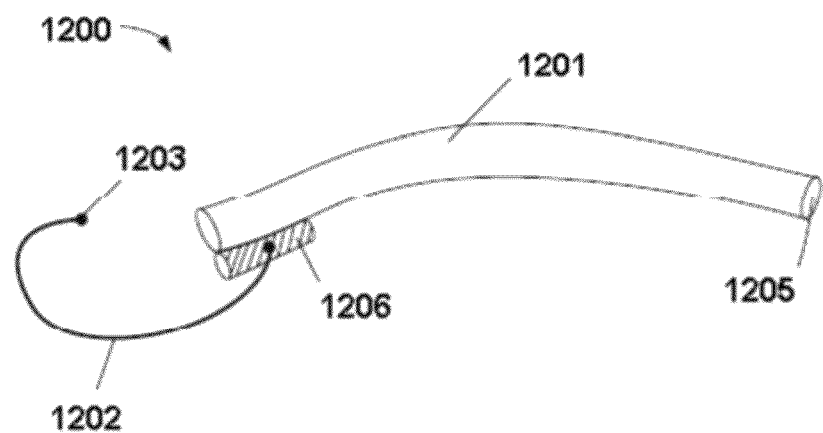

Another embodiment of the implantable device is shown in FIGS. 12A-C. In FIG. 12A, device 1200 includes a non-resorbable drug reservoir portion 1201 that includes a drug reservoir lumen 1205 into which a drug formulation (not shown) is disposed. Attached to the drug reservoir lumen 1205 is a resorbable retention frame lumen 1204. The resorbable retention frame lumen 1204 of device 1200 is connected along its entire length to the drug reservoir lumen 1205, although other configurations are envisioned.

Within the retention frame lumen 1204 is a non-resorbable retention frame 1202 that is a single wire with rounded or blunt end caps 1203 so that the wire has no sharp ends or edges that could negate the tolerability of the segment within the bladder or during voiding. The device 1200 also includes a non-resorbable joint or link 1206 that is connected to the retention frame 1202 and the drug reservoir portion 1201. One end of the retention frame 1202 is anchored in the non-resorbable joint 1206. The rounded or blunt end caps 1203 may assist in securing the retention frame 1202 in the non-resorbable link.

As shown in FIG. 12A, the device initially has a relatively higher profile that facilitates retention of the device during delivery of the drug. As shown in FIG. 12B, the degradation of the retention frame lumen 1204 enables the retention frame 1202 and the drug reservoir portion 1201 to disassociate As a result, the device assumes the low-profile configuration shown in FIG. 12C that is suitable for spontaneous voiding from the bladder during urination.

Figure 13:
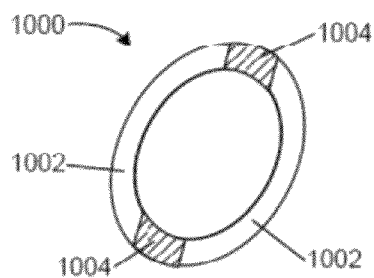
FIG. 13 illustrates three particular embodiments of the drug delivery device shown first in a retention shape in which the reservoir portions are connected by resorbable junctions and then shown in segments suitable for voiding after the junctions have been resorbed.
Figure 13:
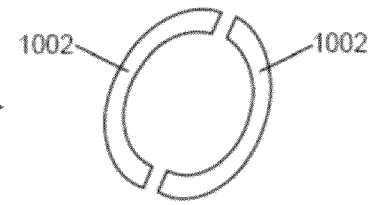
Figure 13:
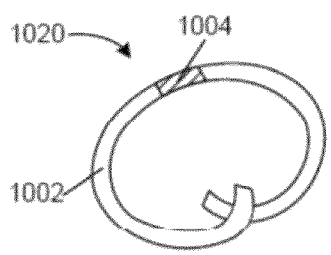
Figure 13:
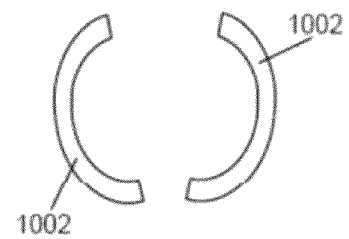
Figure 13:
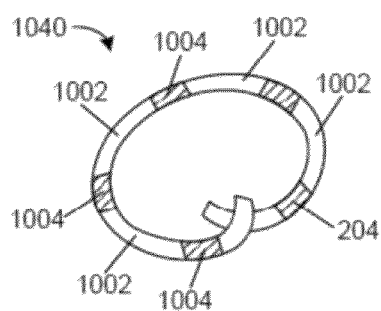
Figure 13:
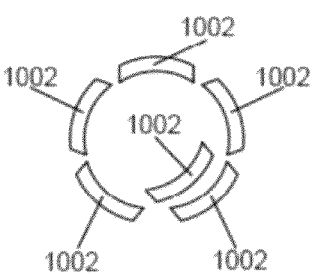

In another aspect of the present disclosure, the device structure is configured to separate into two or more segments, each segment sized and shaped to be excretable from the bladder, upon degradation of at least one degradable link. In embodiments, the drug delivery device can be composed of two or more non-biodegradable drug delivery modules or segments, which are elastomeric or non-elastomeric and connected by one or more biodegradable junctions or links. Examples of these devices are illustrated in FIG. 13. Devices 1000, 1020, and 1040 are shown on the left in their retention shape and on the right in segments suitable for voiding from the bladder. The drug delivery modules 1002 are connected to adjacent modules by resorbable junctions 1004. The drug delivery modules 1002 may be constructed and function like the drug reservoir portions described hereinabove and below.

The devices 1000, 1020, and 1040 initially maintain a retentive shape before degradation/resorption of the junctions causes a loss of mechanical integrity and overall shape change—similarly to the retention frame, wire segments, and links described above with reference to FIGS. 11A-B.

The resorbable junction 1004 may be a biodegradable link. It may be provided in various sizes and shapes, such as plug, sheath, and filament. It may connect two adjacent drug delivery modules by friction fit, molding, suturing, or bonding with medical grade adhesive. Once the junctions go away, each drug delivery module, which is shaped to be tolerable upon voiding, can pass spontaneously during urination. Each module may take a variety of shapes, such as cylindrical, bullet, bulbous, elliptical, circular, oval, bow or other shapes and forms. The overall device shape and the module shapes may vary and take a variety of forms that are tolerable in the bladder. Examples include sphere, ellipsoid, crescent, half-ring, bean, banana, annular, circular, and rectangular shape.

In embodiments, the biodegradable links are positioned in the drug reservoir portion (for example, the drug reservoir lumen), the retention frame portion (for example, the retention frame lumen), or both. Subsequently, the resorbable links or junctions will fail in vivo and remaining device segments or portions will be voided. If needed, a new drug-loaded device may subsequently be implanted. It is also possible to retrieve the device prior to link or junction failure using retrieval devices for this purpose that are known in the art or that can be specially produced.

In other embodiments of the drug delivery device, the device may include a pH-altering agent, a chelating agent, a catalyst, or a combination of these materials.

In embodiments, a pH-altering pill is positioned within the device body, such as within the drug reservoir lumen along with one or more drug tablets. Upon degradation of the release delaying coating or encapsulation on the pH-altering pill, the pH-altering substance is exposed within the device, altering the pH within the device. Portions of the device structure that are pH-responsive may begin degrading thereafter. For example, the device body may be formed from a pH-responsive material, in which case the device body may begin degrading. The device body also may be formed from non-biodegradable portions joined by pH-responsive links, in which case the links may begin degrading. The retention frame or links joining portions of the retention frame may also be formed from pH-responsive materials that begin degrading. Thus, the onset of device elimination is controlled or delayed, such as until after the drug has been released. It should be noted that the device technically begins the degradation process soon after implantation, as the time-delay coating may begin degrading relatively quickly thereafter. However, the time-delay coating may be sufficient to delay release of the pH-altering substance until after the device has released all or a substantial portion of the drug.

Figure 14:
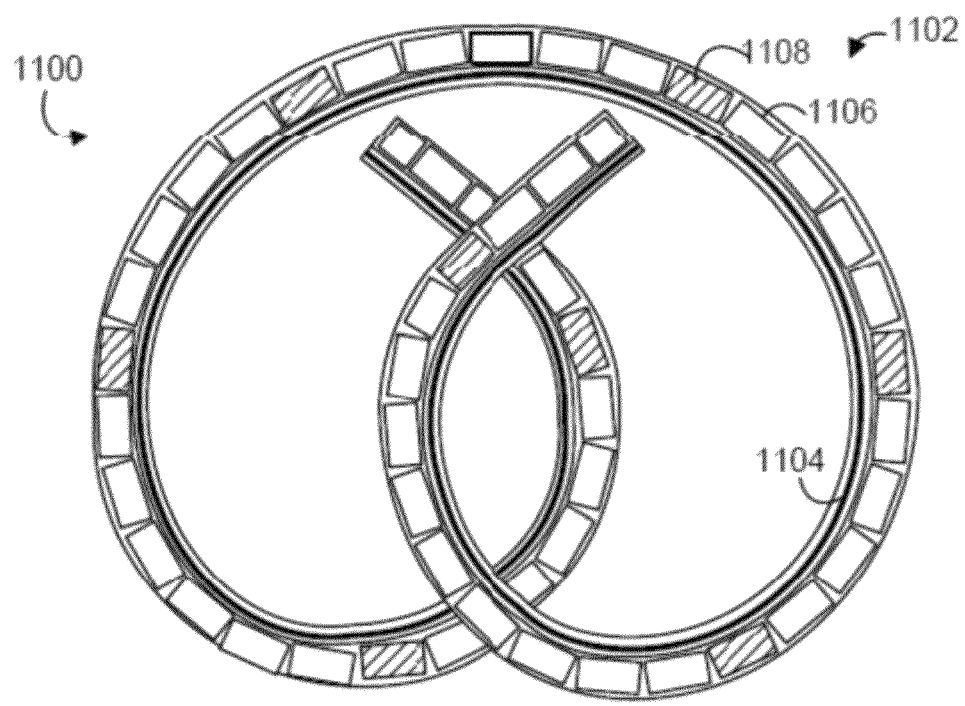
FIG. 14 is a cross-sectional plan view of an embodiment of a self-eliminating drug delivery device.

An example of such a device is shown in FIG. 14. As shown, the device 1100 includes a device body 1102 having a retention frame lumen and a drug reservoir lumen, a retention frame 1104 loaded in the retention frame lumen, and a number of solid drug tablets 1106 loaded in the drug reservoir lumen. A number of pH-altering pills 1108 are interspaced among the solid drug tablets 1106 in the drug reservoir lumen.

During a drug release period, the drug tablets 1106 are solubilized and released into the bladder. The drug tablets 1106 become replaced with urine, which fills the drug reservoir lumen. Also during the drug release period, a coating or encapsulation on the pH-altering pills 1108 begins degrading or dissolving but may not completely degrade or dissolve until the drug release period has substantially or completely ended. The pH-altering pills 1108 then release a pH-altering substance, which alters the pH of the urine in the drug reservoir lumen. The change in pH within the drug reservoir lumen causes the device 1100 to begin an elimination process from the body.

In some embodiments, the device body 1102 may be formed from a pH-responsive polymer, in which case the entire device body 1102 may degrade over the elimination period. In such embodiments, the retention frame 1104 also may be formed from a pH-responsive material, in which case the entire retention frame 1104 may degrade over the elimination period. Alternatively, the retention frame 1104 may be formed from at least two non-biodegradable portions joined by a pH-responsive link, in which case the link may degrade over the elimination period, causing the retention frame 1104 to separate into excretable pieces.

In other embodiments, the device body 1102 may be formed from at least two non-biodegradable portions joined by a pH-responsive link, in which case the links may degrade, causing the device body 1102 to separate into excretable pieces. In such embodiments, the retention frame 1104 also may be formed from a pH-responsive material that degrades, or the retention frame 1104 may be joined by pH-responsive links that degrade over the elimination period.

In still other embodiments, the device body 1102 is not biodegradable, but the retention frame 1104 is formed from a pH-responsive material or includes pH-responsive links, such that the retention frame 1104 degrades or fails over the elimination period. Thereafter, the device body assumes an elongated shape and is excreted from the body. Essentially, a range of configurations can be employed to ensure that all of the device 1100 degrades over the elimination period in response to the change in pH, or that enough of the device degrades so that the remainder of the device can be excreted.

Although the pills 1108 are not shown in the retention frame lumen, a change in pH may occur within the retention frame lumen due to fluid flow into the retention frame lumen, such as through an opening in the device body or through the device body itself. Also, although FIG. 14 is described with reference to a pH-altering pill 1108, time-delayed pills housing other types of agents, such as enzymes, chelating agents, or catalysts, can be employed in association with appropriate materials for the device body and/or degradable links.

Device Dimensions

In one embodiment in which the drug delivery device is designed to be implanted in the bladder, the drug delivery device is designed to be inserted into the bladder through the urethra cystoscopically. Thus, the device may be sized and shaped to fit through a narrow tubular path of a deployment instrument, such as a catheter or cystoscope.

Typically, a cystoscope for an adult human has an outer diameter of about 5 to 7 mm and a working channel having an inner diameter of about 2.4 mm to about 2.6 mm. In other embodiments, a cystoscope has a working channel with a larger inner diameter, such as an inner diameter of 4 mm or more. Thus, the device may be relatively small in size. For example, when the device is elastically deformed to the relatively lower profile shape, the device for an adult patient may have a total outer diameter that is about 3.75 mm or less, such as about 2.6 mm or less. For pediatric patients, the dimensions of the device are anticipated to be smaller. In addition to permitting insertion, the relatively small size of the device may also reduce patient discomfort and trauma to the bladder.

Figure 6:
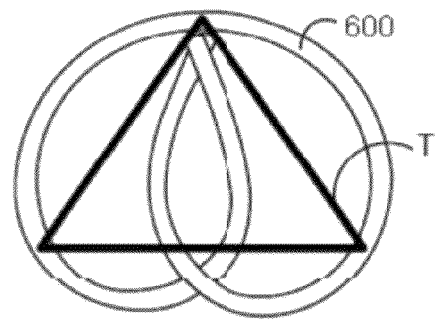
FIG. 6 is an illustration showing the size of an embodiment of a drug delivery device in comparison to an approximation of the bladder trigone region.

The overall configuration of the device preferably is designed to ensure that the device is tolerable to the patient while it is deployed in vivo, as described in U.S. Patent Application Publication No. 2011/0152839 A1 to Cima et al., which is incorporated herein by reference. FIG. 6 shows an example triangle that approximates the trigone of an adult human male. In a human male, the distance from the bladder neck to one of the ureteral orifices is about 2.75 cm and the distance between the two ureteral orifices is about 3.27 cm. Thus, in FIG. 6, the distance from the top vertex to either of the bottom vertices is about 2.8 cm, while the distance between two bottom vertexes is 3.3 cm. The size of the trigone region may vary depending on the animal. In an adult human female, for example, the distance between the two ureteral orifices is about 2.68 cm and the distance from a neck of the bladder to one of the ureteral orifices is about 2.27 cm. Smaller animals may have smaller trigone regions.

The device geometry may be customized to avoid or minimized undesirable contact forces and pressures linked to urgency sensation. Within the three-dimensional space occupied by the device in the retention shape, the maximum dimension of the device in any direction is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm or smaller.

More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, or less. In a preferred embodiment, the device has a dimension in at least one of these directions that is less than 3 cm.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and its exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a position in which the device experiences less compression.

An example of a device that generally satisfies these characteristics is shown in FIGS. 1-5 and 11-14. In particular, the illustrated devices are generally planar in shape even though the device occupies three-dimensional space. Such devices may, define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder, as opposed to a particular bladder location located near the release orifice. However, devices that otherwise move freely within the bladder may be impeded from moving freely when the bladder is empty, and yet the device may still be tolerable if sufficiently compressible as described above.

Device Buoyancy

The device also may have a density that is selected to facilitate floatation in urine, for example in a full bladder. The device has a minimum density in a dry and unloaded state, meaning the device is not loaded with drug and fluid is not present in the device walls or lumens. The density of the device also increases when the device is in a wet state, meaning fluid is present in the device walls and lumens. The device enters the wet state upon implantation in the bladder, as the device becomes surrounded by urine. In use, the device may have a maximum density after implantation, when the device is loaded with the maximum drug payload and liquid displaces any air present in the walls and lumens. Subsequently, the density of the device may remain essentially the same or decrease as the drug is solubilized and released, and replaced by urine.

In general, the device in the dry and loaded state may have a density in the range of about 0.5 g/mL to about 1.5 g/mL, such as between about 0.7 g/mL to about 1.3 g/mL. In some embodiments, the device in the dry and loaded has a density that is less than the density of water, such as a density that is less than about 1 g/mL. Such densities facilitate buoyancy and movement in the bladder. Lighter or lower density materials may be integrated into the device as needed to compensate for any higher density drug or other payload in the device, thereby maintaining an overall density that facilitates buoyancy for tolerance purposes. In addition, air or another gas may be trapped in portions of the device to reduce the overall density. For example, the walls of retention frame lumen may be made impermeable to water such that an air pocket is formed in the retention frame lumen about the elastic wire. A coating or sheath may be applied to the walls, on either the inside or outside, to reduce the water permeability.

One example device may have a mass of about 0.40 grams or less and a density of about 0.7 g/mL or less when unloaded. The device may be loaded with a drug having a mass of about 275 mg or less. In such embodiments, the device when loaded may have a mass of about 0.675 grams or less and a density of about 1.1 g/mL or less. Such a device may be well tolerated in the bladder. Devices of smaller masses and densities would likewise be well tolerated.

In one embodiment, entrapped gas or other buoyancy means are provided at the end portions of the device body. It is believed that this may aid retention of the device in the bladder by keeping the ends from becoming entrained in the bladder neck during urination.

In a preferred embodiment, the drug delivery device is sterilized, such as after the device is manufactured/assembled and before the device is implanted. In some cases, the device may be sterilized after the device is packaged, such as by subjecting the package to gamma irradiation or ethylene oxide gas.

Drug Reservoir Portion

Generally, the drug delivery device includes at least one drug reservoir portion. The drug reservoir portion includes the part of the device body that forms at least one drug reservoir lumen, which houses a drug formulation of at least one drug.

In embodiments, the drug reservoir portion is bounded by a sidewall, and a drug formulation is contained within the resulting drug reservoir lumen. The drug reservoir lumen may comprise an elastic tube. In embodiments, the elastic tube is a polymeric tube. In one embodiment, the drug reservoir lumen of the device includes an elongated tube. An interior of the tube may define one or more drug reservoirs, and a drug formulation may be housed in the drug reservoir(s). In another embodiment, the drug reservoir lumen is in a form other than a tube.

The tube of a drug reservoir lumen may be substantially linear and in some cases may be substantially cylindrical with a circular cross-section, although square, triangle, hexagon, and other polygonal cross-sectional shapes can be used, among others.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

The thickness and strength of certain portions of the drug reservoir portion also may be selected to maintain the retention shape when the device does not include a retention frame. For example, the drug reservoir portion may include a "backbone" that holds the device in its retention shape. The "backbone" may be a thicker and/or stronger section of the material from which the drug reservoir portion is formed. The "backbone" may traverse the length of the drug reservoir portion, either linearly, spirally, or tortuously.

The drug reservoir lumen may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation, as described in further detail below.

In a preferred embodiment, the drug reservoir lumen is formed from a material that is both elastomeric and water permeable. One material that is both elastomeric and water permeable is silicone, although other biocompatible materials may be used.

In embodiments, the drug reservoir portion consists essentially of one or more materials that are bioerodible, either upon contacting a physiological fluid for a desired period of time, or in response to a change in composition of physiological fluid adjacent to or within the device, e.g., change in pH, enzyme presence or concentration. In some embodiments, the device may comprise a sufficient number of dissolvable or degradable links to allow the drug reservoir portion or housing to break down into portions that are small enough to pass through the patient's urethra when voiding without causing pain or discomfort. The device may comprise relatively small portions of non-dissolvable/non-erodible material that break apart and are voided. The small portions of non-erodible/non-dissolvable material may be joined together by degradable links that are dissolvable or erodible upon a change in urine composition about or within the device.

In some embodiments, the entire drug reservoir portion is bioerodible. In one embodiment of a bioerodible device, the device body is formed of a biodegradable or bioresorbable polymer. Examples of suitable such materials include synthetic polymers selected from poly(amides), poly(esters), poly(ester amides), poly(anhydrides), poly(orthoesters), polyphosphazenes, pseudo poly(amino acids), poly(glycerol-sebacate) (PGS), copolymers thereof, and mixtures thereof.

In a preferred embodiment, the resorbable synthetic polymers are selected from polylactic acids), poly(glycolic acids), polylactic-co-glycolic acids), poly(caprolactones), and mixtures thereof. Other curable bioresorbable elastomers include poly(caprolactone) (PC) derivatives, amino alcohol-based poly(ester amides) (PEA) and poly(octane-diol citrate) (POC). PC-based polymers may require additional cross-linking agents such as lysine diisocyanate or 2,2-bis(y-caprolacton-4-yl)propane to obtain elastomeric properties.

In some embodiments, the drug reservoir lumen is non-biodegradable. For example, the drug reservoir lumen shown in FIG. 12 is made from non-biodegradable materials. In these embodiments, other portions of the device structure—for example, the retention frame portion—comprise one or more biodegradable materials. In embodiments, the non-biodegradable drug reservoir lumen may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly (urethanes), celluloses, cellulose acetates, poly(siloxanes), poly(ethylene), poly(tetrafluoroethylene) and other fluorinated polymers, poly(siloxanes), copolymers thereof, and combinations thereof.

In embodiments, the device does not include a retention frame, and the drug reservoir portion is capable of imparting a retention shape to the device. In a particular embodiment, the drug reservoir portion is formed with a material that is treated or altered so that the device is deformable between a retention shape and a deployment shape. For example, the material used to form the drug reservoir portion may "memorize" and spontaneously assume the relatively expanded shape upon the application of heat to the device, such as when exposed to body temperatures upon entering the bladder. In some instances, the heating may cause at least a portion of the polymeric material to cross-link so that the device is capable of retaining the retention shape upon deployment in the bladder.

Figure 2:
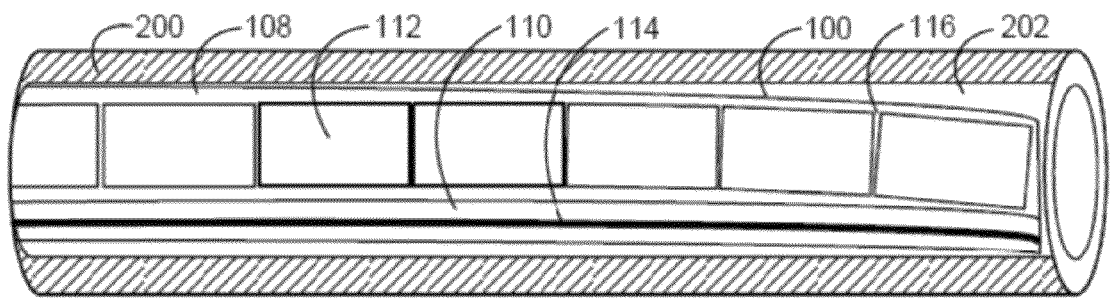
FIG. 2 is a plan view of the drug delivery device shown in FIG. 1, illustrating the drug delivery device inside a deployment instrument.

An example of a drug reservoir portion is shown in FIGS. 1-3. As shown, the drug reservoir portion 102 may include a body formed from an elastomeric tube 122. The tube 122 defines a reservoir 108 that contains a number of drug tablets 112. Ends of the tube 122 may be sealed with sealing structures 120.

At least one aperture 118 may be disposed in the tube 122. In cases in which an aperture 118 is provided, the aperture 118 may be closed by a degradable timing membrane, which may control the initiation of release of the drug formulation from the reservoir. In some cases, a sheath or coating may be positioned about at least a portion of the tube 122 to control or reduce the release rate, such as by reducing the osmotic surface area of the tube or by reducing diffusion through the tube wall. For simplicity, the degradable timing membranes and sheaths or coatings are not shown.

Figure 5:
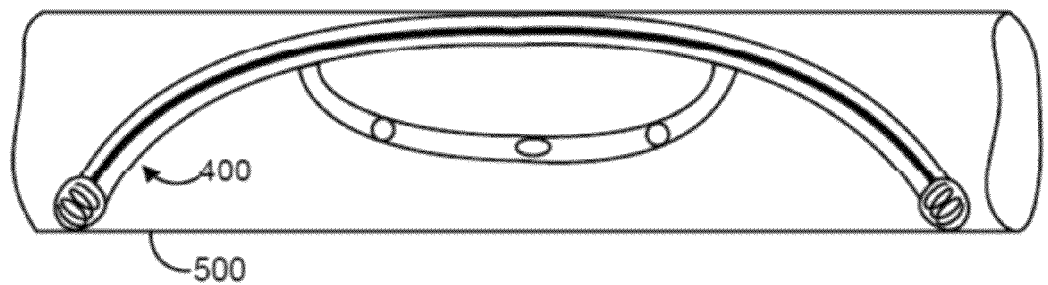
FIG. 5 is a plan view of the drug delivery device shown in FIG. 4, illustrating the drug delivery device inside a deployment instrument.

Another example of such a drug reservoir portion is shown in FIGS. 4 and 5. The drug reservoir lumen 402 has an aperture 414 and the ends of the drug reservoir lumen are sealed with sealing structures 416.

The ends of the tube may be sealed to limit escape of the drug, such as with a sealing structure or other sealing means. The sealing structure may have any shape suited to plug or close the tube end, such as a cylinder 120 as shown in FIG. 1, a ball 416 as shown in FIG. 4, a disk, or others. In some embodiments, the sealing structure may have a larger diameter than the inner diameter of the tube, such that the tube stretches to fit snugly about the sealing structure, closing the tube and retaining the sealing structure in place. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 120 of FIG. 1 that closes the tube end may instead serve as a partition structure to segregate two reservoirs positioned adjacent to each other along the length of the tube. Similarly, the ball-shaped plug 416 of FIG. 4 may serve a similar purpose. The partition may be non-porous or semi-porous, non-resorbable or resorbable and may be formed of a material described above with reference to the cylindrical plug 120 or ball plug 416. The partition also may be formed in the tube, such as by molding. For example, one or more webs may extend through the tube along its length to segregate axial reservoirs that extend along the length of the tube, as shown in Examples J through L of FIG. 8. The partition also may be a structure that joins two different tubes that serve as separate reservoirs, as shown in Examples M through O of FIG. 8.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

In one embodiment, the total volume of the reservoir (or combined reservoirs) is sufficient to contain all the drug needed for local delivery over the course of a single treatment, reducing the number of procedures needed to treat a particular condition.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles. In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Application Publication No. 2009/0149833.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) a combination thereof. In embodiments in which diffusion occurs through the wall, the apertures or passing pores may not be included. In still other embodiments, the device may operate by a combination of osmosis and diffusion.

Apertures

In some embodiments, the device includes one or more apertures or orifices for dispensing the drug, such as via osmosis, diffusion, or a combination thereof, among others.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

In embodiments in which the device includes a device body that defines both drug reservoir and retention frame lumens, such as the embodiment shown in FIG. 3, the aperture or apertures may have various positions on the wall of the drug reservoir lumen with reference to the wall of the retention frame lumen, as further described below.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 µm and about 800 µm, such as between about 25 µm and about 500 µm, and more particularly between about 30 µm and about 400 µm. In one example, the aperture has a diameter between about 100 µm and about 300 µm, such as about 150 µm. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure known in the art.

The apertures may be spaced along a drug reservoir lumen to provide a passageway for release of the drug formulation. The apertures or orifices may be positioned through a sidewall or an end of the drug reservoir lumen. The apertures may be in fluid communication with one or more reservoirs in the drug reservoir lumen. Embodiments of apertures 118 are shown on the drug reservoir portions in FIGS. 1 and 3, respectively. Other embodiments of apertures 414 are shown in FIGS. 4 and 5.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

Degradable Membranes

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the drug reservoir lumen or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). Additional details are described in U.S. Patent Application Publication No. 2009/0149833. In embodiments, degradable membranes may be disposed over any portion of the device, especially degradable materials. The onset of degradation can be delayed by coating degradable portions of the device with a degradable membrane.

The Drug Formulation and Solid Drug Tablets

The drug formulation can include essentially any therapeutic, prophylactic, or diagnostic agent, such as one that would be useful to deliver locally to the bladder or other body cavity or regionally about the body cavity. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. For example, lidocaine base may be released via diffusion through a silicone wall without an aperture, and the release rate may be increased by adding apertures to the wall. Thus, the drug may be formulated to have a high or low solubility depending on the intended release mode. In one embodiment, the drug is formulated to improve its apparent solubility in the implantation environment, such as its apparent solubility in urine within the bladder.

In one embodiment, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocalne, ropivacaine, and trimecaine. Representative examples of aminoesters or ester-class anesthetics include amylocalne, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzyl morphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen; indomethacin, naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In one particular embodiment, the drug delivery device is used in association with the placement of a ureteral stent, such as to treat pain, urinary urgency or urinary frequency resulting from ureteral stent placement. Non-limiting examples of specific drugs for such treatment include anti-muscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutylin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiseptic, antiviral and other anti-infective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the present drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The implantable drug delivery device also may be used to treat neurogenic bladder. Representative examples of drugs for the treatment of neurogenic bladder include analgesics or anaesthetics, such as lidocaine, bupivacaine, mepivacaine, prilocalne, articaine, and ropivacaine; anticholinergics; anti-muscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamitie) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

In a preferred embodiment, the drug formulation is in solid form. For example, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, pellets, or beads, although other configurations are possible. For example, FIGS. 1-3 illustrate a number of the solid drug units 112 loaded into the drug reservoir lumen 108 of the drug delivery device 100, the drug units 112 being suited for implantation.

The drug tablets made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation.

The drug tablet includes a drug content and may include an excipient content. The drug content includes one or more drugs or active pharmaceutical ingredients (API), while the excipient content includes one or more excipients. The term "excipient" is known in the art, and representative examples of excipients useful in the present drug tablets may include ingredients such as binders, lubricants, glidants, disintegrants, colors, fillers or diluents, coatings and preservatives, as well as other ingredients to facilitate manufacturing, storing, or administering the drug tablet.

In order to maximize the amount of drug that can be stored in and released from a given drug delivery device of a selected (small) size, the drug tablet preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely.

The drug formulation may provide a temporally modulated release profile or a more continuous or consistent release profile.

In one embodiment, the drug and excipients are selected and the tablet formulated to be water soluble, so that the drug tablets can be solubilized when the device is located within the vesical, to release the solubilized drug. In a preferred embodiment, the drug tablets are formulated to be sterilizable, either within or outside of the drug delivery device, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery device. For example, the drug tablets may be "mini-tablets" that are much smaller in size than conventional tablets, which may permit inserting the drug tablets through a lumen such as the urethra into a cavity such as the bladder. An embodiment of a solid drug tablet 112 for intravesical insertion or other in vivo implantation is shown in FIGS. 1-3. In a preferred embodiment, the drug tablets are mini-tablets which comprise greater than 80% lidocaine hydrochloride monohydrate.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

The individual drug units may have essentially any selected shape and dimension that fits within the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 112 are substantially cylindrical in shape as shown in FIGS. 1-3 for positioning in the substantially cylindrical drug reservoir lumen 108 shown in FIG. 1. Once loaded, the drug units 112 substantially fill the drug reservoir lumen 108, forming the drug reservoir portion 102.

The drug units may have outer dimensions that are about the same as, are slightly less than, or slightly exceed inner dimensions of the drug reservoir portion. For example, the drug unit 112 shown in FIGS. 1-3 has an outer diameter that is slightly less than an inner diameter of the drug reservoir lumen 108 shown in FIG. 3.

In embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

An example is shown in FIGS. 1-3, which illustrates the drug unit 112 having circular flat end faces and a cylindrical side wall. Thus, the drug unit 112 can be aligned in a row with other drug units 112 for loading into the cylindrical drug reservoir lumen 108 as shown in FIGS. 1 and 2. When so loaded, the drug units 112 substantially fill the drug reservoir lumen 108, with interstices or breaks 116 formed between them to accommodate deformation or movement. The flat end faces permit piecewise flexibility of the device while limiting the volume or space within the drug reservoir portion that is devoted to the interstices or breaks 116. Thus, the device can be substantially filled with solid drug while retaining its flexibility. The tablet uniformity advantageously enables reproducibility in producing the medical product and thereby generally provides reliable, repeatable drug release characteristics.

In some embodiments, each drug unit may have a length that exceeds its width, meaning an aspect ratio of height:width that is greater than 1:1. Suitable aspect ratios for the drug units may be in the range of about 3:2 to about 5:2, although other aspect ratios are possible, including aspect ratios that are less than 1:1, like conventional drug tablets. An example is shown in FIG. 1, which illustrates the drug unit 112 with a length that exceeds its diameter.

In embodiments in which the solid drug tablets are designed for insertion or implantation in a lumen or cavity in the body, such as the bladder, via a drug delivery device, such as a device of the type described above with reference to FIGS. 1-3, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical. An example mini-tablet is shown in FIG. 1. The mini-tablet 112 has a diameter, extending along the end face, in the range of about 1.0 to about 3.2 mm, such as between about 1.5 and about 3.1 mm. The mini-tablet 112 has a length, extending along the side face, in the range of about 1.7 mm to about 4.8 mm, such as between about 2.0 mm and about 4.5 mm. The friability of the tablet may be less than about 2%. Embodiments of solid drug tablets and systems and methods of making the same are further described below with reference to U.S. Patent Application Publication No. 2010/0330149 A1 to Daniel et al., which is incorporated by reference herein.

In a preferred embodiment, the drug tablets include lidocaine. A drug delivery device having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder.

In addition, the drug tablets can be sterilized before or after loading/assembly into a drug delivery device, and the drug tablets possess a commercially reasonable shelf life. Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

Although mini-tablets and other solid drug tablets are described above as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is operable to impart a retention or relatively expanded shape to the device structure, and is deformable between a relatively expanded shape and a relatively lower-profile shape.

For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In embodiments, the device body may include a retention frame lumen, with the retention frame positioned in the retention frame lumen. In certain embodiments, the retention frame portion includes at least one degradable link, the degradation of which causes the retention frame to cease imparting the retention shape to the device structure. In one embodiment, the at least one degradable link is in the retention frame lumen. In some embodiments, the retention frame comprises at least two discrete portions connected together with the at least one degradable link. An example of such a retention frame is shown in FIGS. 11A-B.

In embodiments, the retention frame lumen is formed from a degradable material, and the retention frame is formed for a non-degradable material. An example of such an embodiment is shown in FIGS. 12A-C. In other embodiments, the retention frame lumen and the retention frame are formed from degradable materials.

In a preferred embodiment, the retention frame includes or consists of an elastic wire. In one embodiment, the elastic wire may comprise a biocompatible shape-memory material or a biodegradable shape memory polymer as described in U.S. Pat. No. 6,160,084 to Langer et al. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 1-2, the retention frame 114 is an elastic wire formed from a superelastic alloy, such as nitinol, and surrounded by the wall 124 of the retention frame lumen 110, which forms a protective sheath about the retention frame 114. Thus, the wall 124 may be formed from a polymer material, such as silicone. In other embodiments, the retention frame may be an elastic wire formed from a superelastic alloy, such as nitinol, that is covered in a polymer coating, such as a silicone sheath and is attached to the drug reservoir portion.

In embodiments in which the retention frame comprises a shape-memory material, the material used to form the frame may "memorize" and spontaneously assume the relatively expanded shape upon the application of heat to the device, such as when exposed to body temperatures upon entering the bladder.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIGS. 1 and 4, the device may occupy a space having dimensions suited to impede expulsion from the bladder. When the retention frame is in the relatively lower-profile shape, such as the elongated shapes shown in FIGS. 2 and 5, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

Figure 7:
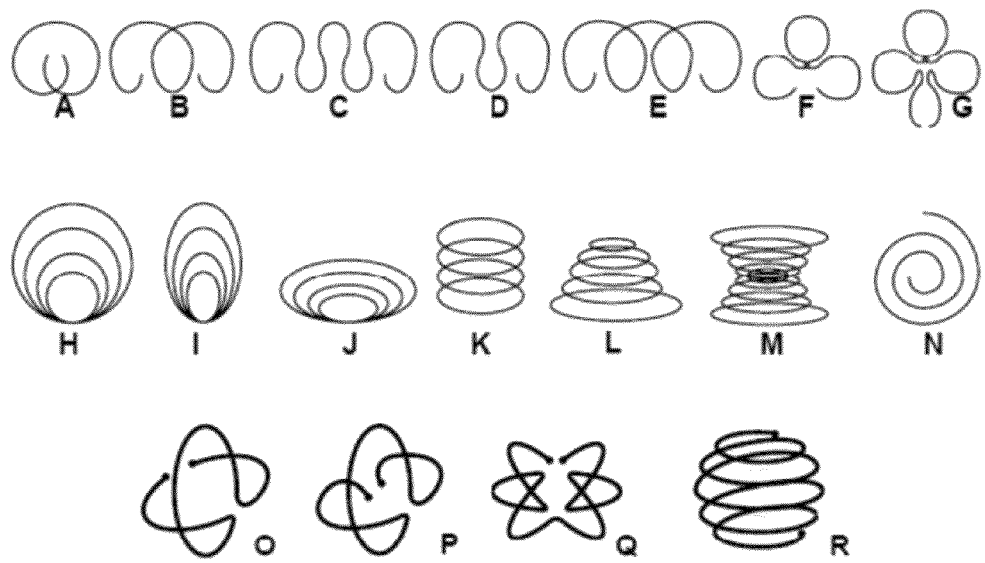
FIG. 7 illustrates examples of shapes for a retention frame of a drug delivery device.

Examples are shown in FIG. 7. The retention frame may have a two-dimensional structure that is confined to a plane, a three-dimensional structure, such as a structure that occupies the interior of a spheroid, or some combination thereof. In particular, Examples A through G illustrate frames comprising one or more loops, curls, or sub-circles, connected either linearly or radially, turning in the same or in alternating directions, and overlapping or not overlapping. Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Examples O through R illustrate retention frame portions that are shaped to occupy or wind about a spherical space, with each retention frame portion shown above a representation of the frame in a sphere. The retention frame portion may generally take the shape of two intersecting circles lying in different planes as shown in Example O, two intersecting circles lying in different planes with inwardly curled ends as shown in Example P, three intersecting circles lying in different planes as shown in Example Q, or a spherical spiral as shown in Example R. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention housing may be omitted, in which case the retention portion may be components of the drug portion itself, which may assume or may be deformed into a retention shape, or the retention portion may be an anchor associated with the drug portion.

Other Device Features

The drug reservoir portion can include a coating or a sheath, which may be substantially impermeable to water or relatively less permeable to water than the drug reservoir portion to reduce or alter the osmotic or diffusive surface area of the device body. Thus, the release rate can be independently controlled or targeted with reduced adjustment of desired device characteristics, such as size, shape, material, permeability, volume, drug payload, flexibility, and spring constant, among others. To achieve the release rate, the coating or sheath may cover all or any portion of the device body, and the coating or sheath may be relatively uniform or may vary in thickness, size, shape, position, location, orientation, and materials, among others and combinations thereof. Further, multiple coatings or sheaths may be provided along different portions of the device body, about the same drug reservoir or different drug reservoirs housing the same or different drug formulations. In cases in which the drug reservoir portion is formed from silicone tubing, for example, a coating may be formed from parylene, while a sheath may be formed from a polymer such as polyurethane or curable silicone, or another biocompatible coating or sheath material known in the art. In some embodiments, the coating or sheath may be positioned on the tube between the end and the orifice so that water permeating through the tube adjacent to the end can drive through the portion of the tube covered by the sheath and out of the orifice, reducing or avoiding isolation or stagnation of the drug under the sheath. Coatings and sheaths, and equations for selecting such designs, are described in U.S. Patent Application Publication No. 2009/0149833.

In one embodiment, the device includes at least one radio-opaque portion or structure to facilitate detection or viewing (e.g., by X-ray imaging or fluoroscopy) of the device by a medical practitioner as part of the implantation or retrieval procedure. In one embodiment, the tube is constructed of a material that includes a radio-opaque filler material, such as barium sulfate or another radio-opaque material known in the art. Some tubing may be made radio-opaque by blending radio-opaque fillers, such as barium sulfate or another suitable material, during the processing of the tubing. The radio-opaque material also may be associated with the retention frame. For example, a platinum wire may be wound about ends of the elastic wire and covered in smoothening material. As shown in FIG. 4, a platinum wire 410 is coiled at the ends of the elastic wire 406, and coated with a smoothening material 412. Ultrasound imaging may be used. Fluoroscopy may be the preferred method during deployment/retrieval of the non-erodible device by providing accurate real-time imaging of the position and orientation of the device to the practitioner performing the procedure.

Combination of the Components

Figure 8:
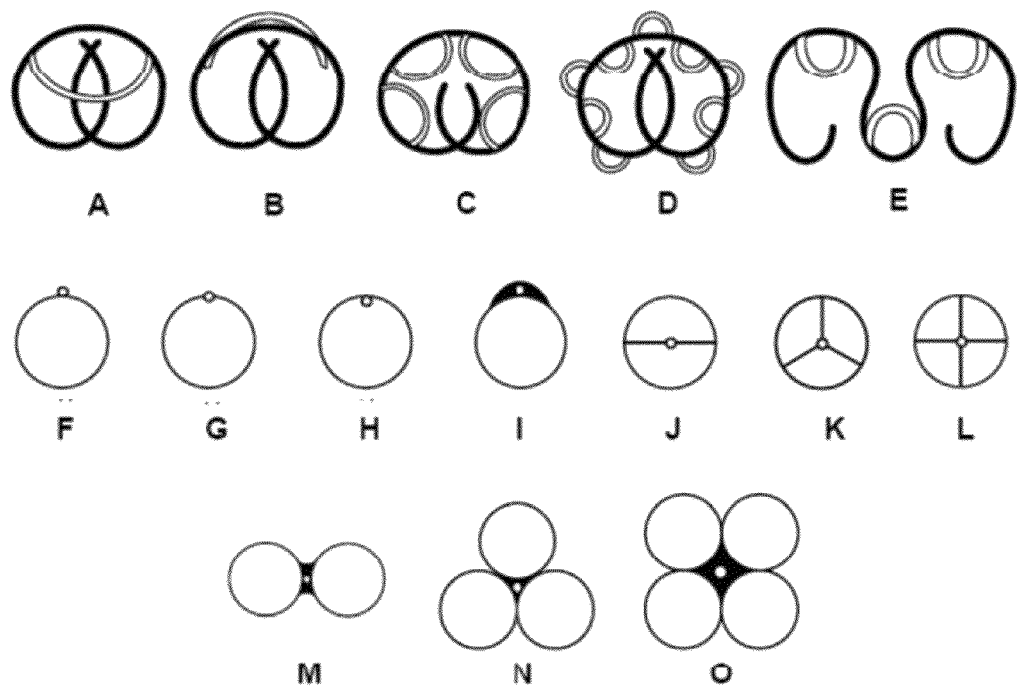
FIG. 8 illustrates examples of configurations for drug delivery devices having at least one drug delivery portion and a retention frame portion.

The drug reservoir portion and the retention frame portion are associated with each other to form the drug delivery device. A variety of different associations are envisioned. For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 1-3. FIG. 8 also illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion may be attached to only portion of the retention frame. The drug reservoir portion may have first and second end portions that are attached to an portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion. Examples A through E of FIG. 8 illustrate such embodiments.

In other embodiments, the drug reservoir portion and the retention frame portion may be the same component in some embodiments. In such cases, the device may comprise a tube formed in a configuration having a sufficient spring constant to retain the device in the body, as described above. Also, the drug reservoir portion may be wrapped around the retention frame portion, one or any number of times.

The embodiments described herein may be combined and varied to produce other drug delivery devices that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

Furthermore, when the device is in the retention shape, the retention frame portion may have any orientation with reference to the drug reservoir portion, lying either inside, outside, above, or below the drug reservoir portion or moving with reference to the drug reservoir portion as the device moves through the implantation site. For example, the device 100 includes a retention frame portion that lies inside the perimeter of the drug reservoir portion. In other embodiments, the device includes a retention frame portion that lies below the drug reservoir portion (such that the retention frame portion would not be visible in FIG. 1). A particular orientation between the two portions can be maintained by filling the retention frame portion with a filling material, such as a silicone adhesive, after the retention frame is loaded. The filling material may cure or solidify to prevent movement of one portion with reference to the other. Other means of maintaining the orientation of the retention frame portion with reference to the drug reservoir portion also can be used.

The aperture may be positioned inside the perimeter of the device, outside of the perimeter of the device, or an upper or lower plane of the device. For example, the device 100 includes an aperture 118 located on an outside perimeter of the device, but in other embodiments the aperture is located on an upper plane of the device. An aperture positioned on the inside perimeter or on the upper or lower plane of the device advantageously may be less likely to become positioned directly adjacent to a portion of the implantation site, such as the bladder wall, delivering a large quantity of drug to one particular location. The aperture also may be formed in a groove or indent defined between the walls of the drug reservoir portion and the retention frame portions, so that the walls serve as bumpers that impede the aperture from becoming positioned directly adjacent to the implantation site. For example, the aperture 118 of the device 100 could instead be formed in a groove or indent between the walls 122 and 124.

For ease of manufacturing, the aperture may be formed through the wall of the drug reservoir portion on an opposite side from the retention frame portion, as shown in FIG. 3. When the aperture is positioned opposite from the retention frame portion, it may be desirable to secure the retention frame portion below the device as described above, so that the aperture becomes positioned above the device, reducing the risk of the aperture becoming positioned on the outside perimeter of the device. However, other configurations are possible.

It should be noted that the device 600 shown in FIG. 6 has a slightly different shape and configuration than the device 100 shown in FIG. 1. For example, the ends of the device 600 are relatively straighter than the ends of device 100. The straighter ends may result because the retention frame of the device 600 has relatively straight end portions, while the retention frame of the device 100 has relatively curved end portions. A retention frame with relatively straight end portions may be less likely to puncture the walls of the device body during drug loading and thereafter, reducing the risk of device failure after implantation. However, either retention frame shape can be used.

In the embodiment shown in FIG. 1, for example, the drug delivery device 100 is suited for delivering a drug into the bladder. The drug reservoir lumen 108 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 108 may hold about 10 to 100 cylindrical drug tablets, such mini-tablets. The mini-tablets may each having a diameter of about 1.0 to about 3.3 mm, such as about 1.5 to about 3.1 mm, and a length of about 1.5 to about 4.7 mm, such as about 2.0 to about 4.5 mm. Such mini-tablets may have a lidocaine payload of about 3.0 to about 40.0 mg. One particular example of a mini-tablet may have a diameter of about 1.52 mm, a length of about 2.0 to 2.2 mm, and a mass of about 4.0 to 4.5 mg lidocaine. Another particular example of a mini-tablet may have a diameter of about 2.16 mm, a length of about 2.9 to 3.2 mm, and a mass of about 11.7 to 13.1 mg lidocaine. Yet another particular example of a mini-tablet may have a diameter of about 2.64 mm, a length of about 3.5 to 3.9 mm, and a mass of about 21.3 to 23.7 mg lidocaine. Still another particular example of a mini-tablet may have a diameter of about 3.05 mm, a length of about 4.1 to 4.5 mm, and a mass of about 32.7 to 36.9 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer, filling material, or buoyancy material.

The foregoing specific configurations are merely possibilities of the type of devices that may be created by a person skilled in the art upon reading the present disclosure. For example, in some embodiments the drug reservoir portion may be omitted completely, and the retention frame portion may be associated with another component for retention in the bladder. Examples of other components include diagnostic equipment, test materials, and small electronic devices, such as cameras and sensors, among others.

III. Method of Making the Device

An embodiment of a method of making an implantable drug delivery device may include forming a drug delivery device, forming a number of drug tablets, and loading the drug tablets into the drug delivery device. In embodiments, forming the drug delivery device may include one or more of the following sub-steps: forming a device body, forming a retention frame, associating the device body with the retention frame, and forming one or more apertures in the body. In other embodiments, forming the drug delivery device may include one or more of the following sub-steps: forming a device body capable or maintaining a retention shape, and forming one or more apertures in the device body. In further embodiments, forming the drug delivery device may include one or more of the following sub-steps: forming a device body, treating the device body so that it will maintain a retention shape, and forming one or more apertures in the device body.

Forming the device body may include forming a flexible body having walls that define a drug reservoir lumen and, if necessary, a retention frame lumen. For example, the device body may be formed by extruding or molding a polymer, such as silicone. In particular, forming the device body may include integrally forming two tubes or walls that are substantially aligned and adjoined along a longitudinal edge. Alternatively, the two lumens may be separately formed and attached to each other, such as with an adhesive. Other methods of forming the device body also may be employed.

Forming a retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the retention frame may be formed by forming the elastic wire into a pretzel shape and heat treating the elastic wire at a temperature over 500° C. for a period over five minutes. In embodiments in which the retention frame comprises a low modulus elastomer, the step of forming the vesical retention frame may comprising forming one or more windings, coils, loops or spirals in the frame so that the frame functions as a spring. For example, the retention frame may be formed by extrusion, liquid injection molding, transfer molding, or insert molding, among others. Similar techniques may be used to form a device body capable of assuming a retention shape without being associated with a retention frame.

Associating the device body with the retention frame may comprise inserting the retention frame into the retention frame lumen of the device body. In some embodiments, a distal end of the retention frame is blunted or is covered in a smooth ball of increased cross section during insertion of the retention frame into the lumen. The ball may facilitate driving the retention frame through the retention frame lumen without puncturing the wall of the device body. Also in some embodiments, the device body may be slightly compressed between two surfaces during the insertion of the retention frame. Compressing the device body elongates the opening into the retention frame lumen, facilitating loading.

In some embodiments, associating the device body with the retention frame further includes filling the retention frame lumen with a filling material after the retention frame is loaded. The filling material occupies the remainder of the lumen not occupied by the retention frame, reducing the ability of the device body to stretch along, or twist or rotate about, the retention frame. For example, silicone or another polymer may be injected or poured into the retention frame lumen and may cure therein. In other embodiments, associating the device body with the retention frame portion may comprise integrally forming the two portions together, such as by overmolding the device body about the retention frame.

Forming one or more apertures in the device body may include laser drilling or mechanically punching one or more holes in the device body.

The drug tablets made by a direct compression tableting process, a molding process, or other processes known in the pharmaceutical arts. The drug tablets may be loaded into the drug delivery device by any known method, including those described in U.S. Patent Application Publication No. 2010/0331770 A1 to Lee et al., which is incorporated herein by reference.

Some steps or sub-steps of the method of making an implantable drug delivery device may be performed in other orders or simultaneously. For example, the retention frame may be associated with the device body either before or after the drug units are loaded into the device body. Similarly, the apertures may be formed in the device body either before or after the drug tablets are loaded.

In embodiments, the method of making an implantable drug delivery device may further include partitioning the drug reservoir lumen into multiple discrete drug reservoirs, such as by positioning one or more partition structures within the drug reservoir lumen in an alternating fashion with the loading of the drug tablets. In embodiments, the method may further include sealing the drug tablets in the device body. The method may also include associating one or more release controlling structures with the drug reservoir lumen, such as a sheath or coating placed over at least a portion of the surface of the device body to control the rate of release of the drug or a degradable membrane positioned over or in one or more of the apertures to control the initial time of release of the drug therethrough.

IV. Use and Applications of the Device

The device may be implanted in the bladder or other body cavity or lumen of a patient in need thereof. Subsequently, the device may release one or more drugs for the treatment of one or more conditions, locally to one or more tissues at the deployment site and/or regionally to other tissues distal from the deployment site. The release may be controlled over an extended period. Thereafter, the device may be resorbed, excreted, or some combination thereof.

Figure 9:
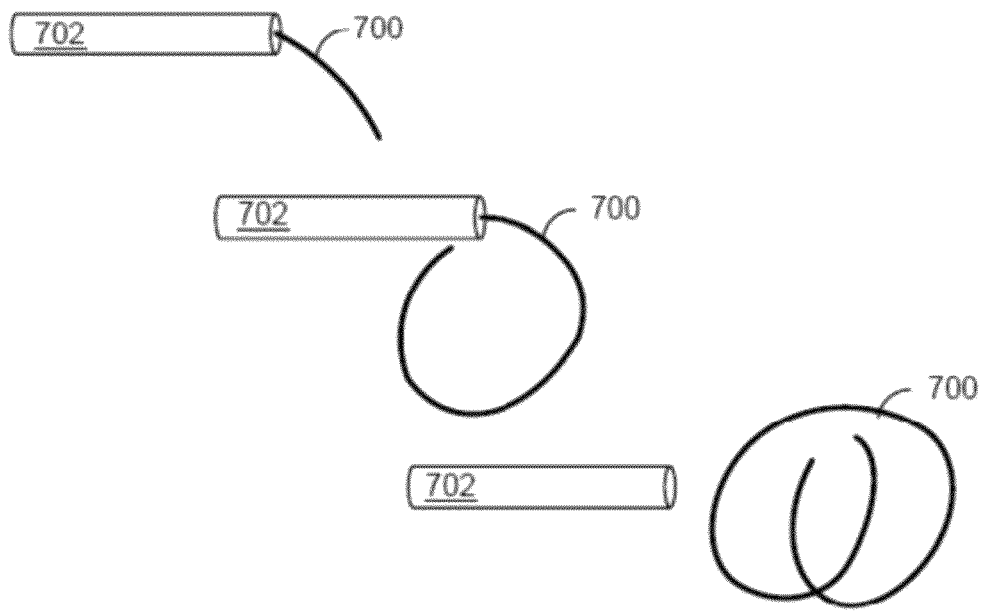
FIG. 9 illustrates a method of implanting a drug delivery device.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 9, which shows the device 700 assuming a retention shape as the device exits a deployment instrument 702. The deployment instrument 702 may be any suitable lumen device, such as a catheter, urethral catheter, or cystoscope. These terms are used interchangeably herein, unless otherwise expressly indicated. The deployment instrument 702 may be a commercially available device or a device specially adapted for the present drug delivery devices.

Once implanted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

Figure 10:
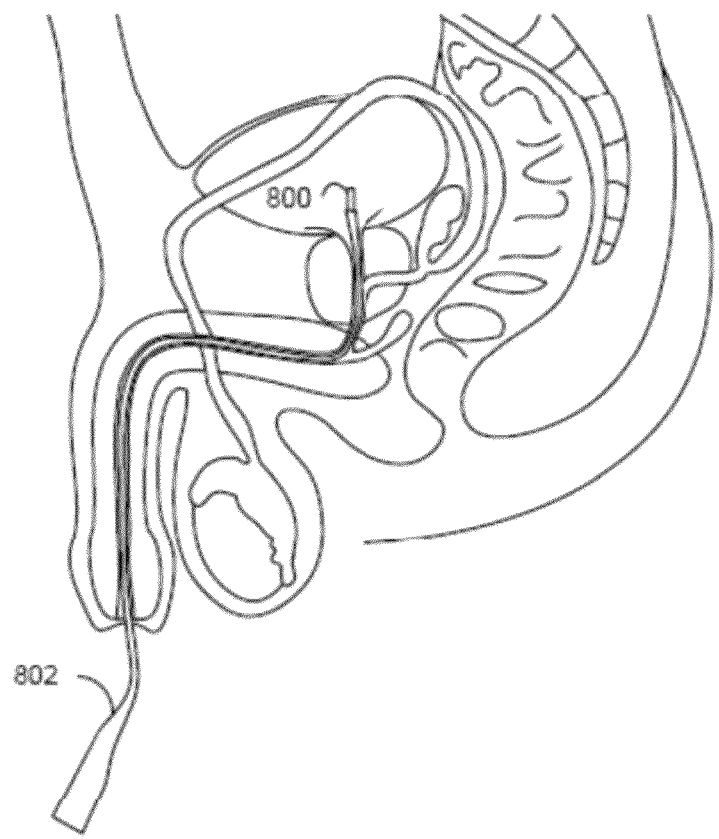
FIG. 10 is a sagittal view of a male patient, illustrating a drug delivery device exiting a deployment instrument into the bladder of the patient.

FIG. 10 illustrates the implantation of a device 800 into the bladder, wherein the adult male anatomy is shown by way of example. A deployment instrument 802 may be inserted through the urethra to the bladder, and the device 800 may be passed through the deployment instrument 802, driven by a stylet or flow of lubricant or other fluid, for example, until the device 800 exits into the bladder. Thus, the device is implanted into the bladder of a male or female human patient in need of treatment, either adult or child.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the intravesical drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

In one embodiment, the intravesical drug delivery device is implanted into a bladder to locally deliver a local anesthetic agent for management of pain arising from any source, such as a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In one particular embodiment, a device having a payload of lidocaine may be delivered to the bladder, and lidocaine may be continuously released from the device over an extended period. Implanting lidocaine in solid form permits further reducing the size of the device to reduce bladder irritation and patient discomfort. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device.

V. Methods of Device Removal

In another aspect, a method is provided for eliminating the drug delivery device from the bladder, preferably following release of its drug payload. The method may include changing the composition of urine in the bladder to trigger degradation of at least part of the device structure to enable the device structure or parts thereof to be excreted from the bladder. In embodiments, changing the composition of urine in the bladder is delayed so that the device structure maintains a bladder retention shape until after the drug formulation has been released.

In one embodiment, the device includes a housing that contains a drug, and following release of some or all of the drug from the housing, the method includes dissolving or eroding the housing sufficiently so that it may be excreted from the bladder, wherein the dissolving or eroding is induced by the physician, nurse, medical technician, or patient by changing the pH of the urine by administering to the patient at least one selected substance in an amount effective to change the pH of the urine. The introduction may occur by an orally administered substance, by use of an instillation procedure to instill into the bladder the agent that changes the pH of the urine or chemically erodes the device, or by releasing an agent or substance from a release delayed tablet or capsule within the device, the agent initiating degradation of the device. The induction may occur for example after release of the solubilized drug has been substantially completed.

In some embodiments, changing the composition of the urine in the bladder comprises releasing from the device a pH-altering agent, a chelating agent, or a catalyst into the urine. The pH of the urine should be changed to a value effective to cause at least a portion of the device structure to degrade. In other embodiments, the device itself comprises a pH-altering agent that is released into the urine following a release delay period. The pH-altering agent may be contained in at least one solid unit operable to release the pH-altering agent into the urine following a release delay period, and the solid unit may be coated or encapsulated with a release delaying material effective to delay release of the pH-altering agent for the release delay period.

After the drug has been delivered from the housing, the housing, or at least a portion of the housing, may be dissolved or eroded by changing the pH of urine in the bladder or within the device. For example, the housing may dissolve when the urine attains an acidic pH or a basic pH. In some embodiments, the housing may dissolve when the urine attains a pH of 6 or less, 5.5 or less, 5 or less, 4.5 or less, 4 or less, 3.5 or less, or 3 or less. In other embodiments, the housing may dissolve when the urine attains a pH of 8 or more, 8.5 or more, 9 or more, 9.5 or more, 10 or more, 10.5 or more, or 11 or more.

In a preferred embodiment, the pH of the urine in the bladder or within the device may be changed after completion of a drug treatment schedule. In one embodiment, the pH of the patient's urine may be changed after all or most of the drug is delivered from device. For example, the change in pH may be provoked after the device delivers the desired dose of drug over an extended period of time, e.g., 24 hours, 5 days, 7 days, 10 days, 14 days, or 20, 25, 30, 45, 60, or 90 days, or more. In one embodiment, the change in pH may be provoked by administering to the patient a substance, e.g., a drug or supplement or particular food, that results in a change in pH of urine in the bladder. The change in pH also may be provoked by a change in diet. The change in pH also may be provoked by releasing a pH altering substance from within the device, such as upon degradation or dissolution of a release delaying coating or encapsulation. The end point of the pH change is sufficient to cause the deployed device to dissolve or erode in the urine.

Accordingly, in some embodiments, dissolution or erosion of the housing may be provoked by administering to the patient a substance that increases urine pH such as acetazolamide, potassium citrate, or sodium bicarbonate. Alternatively, dissolution or erosion of the housing may be provoked by administering to the patient a substance that decreases urine pH such as ammonium chloride, thiazide diuretics, and methenamine mandelate. Also, the patient's urine may be made more acidic by changing the patient's diet, such as by changing the patient's diet to a diet rich in meats and/or cranberries. The patient's urine may be made more alkaline by changing the patient's diet, such as by changing the patient's diet to a diet rich in citrus fruits, legumes, and vegetables. The patient may consume the substance or remain on the diet for a period of time sufficient to cause complete dissolution or erosion and voiding of the housing, e.g., 24 hours, 48 hours, 3 days, 5 days, or 7 days.

In another embodiment, the patient may be administered a substance and/or placed on a diet that maintains the patient's urine in an acidic or basic state during the course of drug delivery. The pH of the patient's urine then may be changed at the end of the drug therapy, e.g., after all or most of the drug is delivered from device, to cause the device to erode or dissolve. The change in pH may be provoked by changing the patient's diet, ending treatment of the pH-altering substance, or administering a different substance to alter the urine's pH. For example, during the course of drug treatment, the patient may be administered a substance and/or placed on a diet to maintain a basic urine pH. At the end of the treatment, the patient may be administered a substance and/or placed on a diet to provoke an acidic urine pH that causes the device to dissolve or erode. Alternatively, during treatment, the patient may be administered a substance and/or placed on a diet to maintain an acidic urine pH. At the end of the treatment, the patient may be administered a substance and/or placed on a diet to provoke a basic urine pH that causes the device to dissolve or erode. In some embodiments, a material may be used that is water soluble at a neutral pH but water insoluble at an acidic or basic pH, and the patient's urine may be maintained in an acidic or basic state during the course of drug therapy to prevent dissolution or erosion of the device. Upon completion of the drug therapy, the patient's urine may be allowed to return to a normal, pH-neutral state to cause dissolution or erosion of the device or a portion of the device.

In another embodiment, the drug delivery device may comprise a material that will degrade or erode when contacted by an enzyme. The device may be deployed into a lumen of the patient, such as the patient's bladder, and the drug may be solubilized within the housing and released from the housing into the patient's lumen. After the drug has been delivered from the housing, the housing, or at least a portion of the housing, may be dissolved or eroded by introducing an enzyme into contact with a reactable portion of the device body.

In one embodiment, the enzyme may be introduced into the bladder after completion of a drug treatment schedule. In one embodiment, the enzyme may be introduced after all or most of the drug is delivered from device. For example, the enzyme may be introduced after the device delivers the desired dose of drug over an extended period of time, e.g., 24 hours, 5 days, 7 days, 10 days, 14 days, or 20, 25, 30, 45, 60, or 90 days, or more. In one embodiment, the enzyme may be naturally produced by the patient in one embodiment, the enzyme may be produced by the patient in response to a substance administered to the patient. In another embodiment, the enzyme may be administered to the patient at or near the end of treatment, e.g., administered directly into the bladder or other body lumen in which where the device is deployed. In yet another embodiment, the enzyme may be released from a pill housed in the device, such as a tablet or capsule having a release delaying coating or encapsulation.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable medical device for controlled drug delivery, comprising:
    a device structure which comprises a device body having at least one drug reservoir lumen, the device structure being deformable between a retention shape and a low profile shape for deployment in the bladder of a patient; and
    a drug formulation positioned in the drug reservoir lumen, the drug formulation comprising at least one drug,
    wherein the device comprises a retention frame lumen having a retention frame therein, the retention frame operable to impart the retention shape, and
    wherein the retention frame comprises two or more wire segments connected by at least one degradable link, the at least one degradable link being located within the retention frame lumen and configured to degrade at a selected time in vivo to cause the retention frame to cease imparting the retention shape and thereby permit the device structure to assume the low profile shape suited for excretion from the bladder.

2. The implantable medical device of claim 1, wherein the device body comprises an elastic, polymeric tube, the tube having a sidewall which defines the drug reservoir lumen.

3. The implantable medical device of claim 1, wherein at least a portion of the device body comprises silicone.

4. The implantable medical device of claim 1, wherein the device body comprises at least one aperture in fluid communication with the drug reservoir lumen.

5. The implantable medical device of claim 1, wherein the drug formulation comprises a plurality of solid drug tablets.

6. The drug delivery device of claim 1, wherein the wire segments are formed of nitinol or another superelastic alloy.

7. The drug delivery device of claim 1, wherein the wire segments are formed of a resorbable material.

8. The drug delivery device of claim 1, wherein the device body is formed of silicone or another elastomeric polymer.

9. The drug delivery device of claim 1, wherein the wire segments comprise rounded or blunt end caps.

10. An implantable medical device for controlled drug delivery, comprising:
    a device structure having at least one drug reservoir lumen and a retention frame lumen, the device structure being deformable between a retention shape and a low profile shape for deployment in the bladder of a patient;
    a retention frame positioned in the retention frame lumen, the retention frame comprising at least two discrete portions connected together with at least one degradable link located within the retention frame lumen and being operable to impart the retention shape to the device structure;

a drug formulation positioned in the at least one drug reservoir lumen, the drug formulation comprising at least one drug;

wherein the device structure is configured to assume a flexible elongated shape upon degradation of the at least one degradable link following a selective alteration of a composition of urine in contact with the degradable link in vivo, the degradation of the at least one degradable link being effective to cause the device structure to lose the retention shape and assume the flexible elongated shape, while remaining only a single structure, so that the device is excretable from the bladder.

11. The implantable medical device of claim 10, wherein at least a portion of the device structure is formed of a material selected to degrade following a selected change in the pH of the physiological fluid.

12. The implantable medical device of claim 10, wherein at least a portion of the device structure is formed of a material selected to degrade following introduction of a catalyst into the physiological fluid.

13. The implantable medical device of claim 10, wherein at least a portion of the device structure is formed of a material selected to degrade following introduction of a chelating agent into the physiological fluid, the chelating agent being effective to bind to an inhibitory ion which then allows an enzyme to degrade the at least one portion of the device structure.

14. The implantable medical device of claim 10, wherein the device structure is associated with at least one fluid-altering agent effective to cause the selective alteration of the composition of the fluid adjacent to or within the device structure.

15. The implantable medical device of claim 14, wherein the at least one fluid-altering agent is contained in at least one solid unit operable to release the fluid-altering agent into the physiological fluid upon conclusion of a release delay period.

16. The implantable medical device of claim 15, wherein the solid unit is coated or encapsulated with a release delaying material.

17. The implantable medical device of claim 15, wherein the fluid-altering agent comprises one or more of the following: a pH-altering agent, a chelating agent, or a catalyst.

18. The implantable medical device of claim 10, wherein the device structure comprises an elastic, polymeric tube, the tube having a sidewall which defines the drug reservoir lumen.

19. The implantable medical device of claim 10, wherein the device structure comprises at least one aperture in fluid communication with the drug reservoir lumen.

20. The implantable medical device of claim 10, wherein the drug formulation is in the form of a plurality of solid drug tablets.

21. A drug delivery device for controlled drug delivery in the bladder of a patient, comprising:
a device body which is deformable between a coiled retention shape and a low profile shape for deployment in a bladder of a patient, the device body comprising
a drug reservoir lumen containing a drug formulation, and
a retention frame lumen having a retention frame therein, the retention frame imparting the coiled retention shape to the device body;
wherein the retention frame comprises two or more wire segments connected by at least one degradable link, the at least one degradable link being located within the retention frame lumen and configured to degrade at a selected time following insertion into the bladder, to cause the device body to lose the coiled retention shape, while the device body remains only a single structure, to permit the device body to be excreted from the bladder.

22. The drug delivery device of claim 21, wherein the wire segments are formed of nitinol or another superelastic alloy.

23. The drug delivery device of claim 21, wherein the wire segments are formed of a resorbable material.

24. The drug delivery device of claim 21, wherein the device body is formed of silicone or another elastomeric non-biodegradable polymer.

25. The drug delivery device of claim 21, wherein the wire segments comprise rounded or blunt end caps.

* * * * *